(12) United States Patent
Belyk et al.

(10) Patent No.: US 7,754,731 B2
(45) Date of Patent: Jul. 13, 2010

(54) POTASSIUM SALT OF AN HIV INTEGRASE INHIBITOR

(75) Inventors: Kevin M. Belyk, Somerset, NJ (US); Henry G. Morrison, Simi Valley, CA (US); Amar J. Mahajan, Piscataway, NJ (US); Daniel J. Kumke, Colts Neck, NJ (US); Hsien-Hsin Tung, Edison, NJ (US); Lawrence Wai, Scotch Plains, NJ (US); Vanessa Pruzinsky, Metuchen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1195 days.

(21) Appl. No.: 11/293,678

(22) Filed: Dec. 2, 2005

(65) Prior Publication Data

US 2006/0122205 A1 Jun. 8, 2006

Related U.S. Application Data

(60) Provisional application No. 60/633,132, filed on Dec. 3, 2004.

(51) Int. Cl.
*C07D 239/54* (2006.01)
*A61K 31/515* (2006.01)

(52) U.S. Cl. .................................. 514/269; 544/319
(58) Field of Classification Search ................. 544/319; 514/269
See application file for complete search history.

(56) References Cited

U.S. PATENT DOCUMENTS

| | | | |
|---|---|---|---|
| 5,413,999 A | 5/1995 | Vacca et al. | |
| 5,527,799 A | 6/1996 | Vacca et al. | |
| 5,668,132 A | 9/1997 | Vacca et al. | |
| 5,717,097 A | 2/1998 | Vacca et al. | |
| 6,140,362 A * | 10/2000 | Michelotti et al. | 514/514 |
| 6,472,404 B1 | 10/2002 | Martin et al. | |
| 6,620,841 B1 | 9/2003 | Fujishita et al. | |
| 6,645,956 B1 | 11/2003 | Fujishita et al. | |
| 7,098,201 B2 | 8/2006 | Fujishita et al. | |
| 7,169,780 B2 | 1/2007 | Crescenzi et al. | |
| 7,176,220 B2 | 2/2007 | Satoh et al. | |
| 7,217,713 B2 | 5/2007 | Crescenzi et al. | |
| 7,241,794 B2 | 7/2007 | Dunn et al. | |
| 7,354,932 B2 | 4/2008 | Bridger et al. | |
| 7,354,934 B2 | 4/2008 | Bridger et al. | |
| 7,414,045 B2 | 8/2008 | Crescenzi et al. | |
| 7,435,734 B2 | 10/2008 | Crescenzi et al. | |
| 2004/0058999 A1 | 3/2004 | Tarro | |
| 2006/0046985 A1 | 3/2006 | Crescenzi et al. | |
| 2006/0217413 A1 | 9/2006 | Satoh et al. | |
| 2008/0167341 A1 | 7/2008 | Bridger et al. | |
| 2008/0176869 A1 | 7/2008 | Crescenzi et al. | |
| 2008/0275004 A1 | 11/2008 | Crescenzi et al. | |

FOREIGN PATENT DOCUMENTS

| | | |
|---|---|---|
| WO | WO 03/035077 A1 | 5/2003 |
| WO | WO 2006/060681 A2 | 6/2006 |
| WO | WO 2006/060711 A2 | 6/2006 |
| WO | WO 2006/060731 A2 | 6/2006 |

OTHER PUBLICATIONS

Marcus et al., PubMed Abstract (Intervirology 45(4-6):260-6), 2002.*
van Heeswijk et al., PubMed Abstract (Antivir Ther. 6(4):201-29) Dec. 2001.*
Lasky, L. A., et al., "Delineation of a Region of the Human Immunodeficiency Virus Type 1 gp120 Glycoprotein Critical for Interaction with the CD4 Receptor", Cell, vol. 50, pp. 975-985 (1987).
Li, T. "Materials Engineering of Solid-State Dosage Forms", Pharmaceutical Research, 2007, vol. 25, pp. 949-952.
Kanatzidis, M. et al. "Report from the third workshop on future directions of solid-state chemistry: The status of solid-state chemistry and its impact in the physical sciences", Progress in Solid State Chemistry, 2007, vol. 36, pp. 1-133.
Declaration of Michael Miller filed Dec. 26, 2006 in U.S. Appl. No. 11/491,815, now US 7217713.
Dean et al. "Genetic Restriction of HIV-1 Infection and Progression to AIDS by a Deletion Allele of the CKR5 Structural Gene", Science, 1996, vol. 273, pp. 1856-1862.
Fauci et al. "Acquired Immunodeficiency Syndrome: Epidemiologic, Clinical, Immunologic, and Therapeutic Considerations", Annals of Internal Medicine, 1994, vol. 100, pp. 92-106.
Vacca et al. "L-735,524: An orally bioavailable human immunodeficiency virus type 1 protease inhibitor", Proc. Natl. Acad. Sci. USA, 1994, vol. 91, pp. 4096-4100.
"HIV & AIDS in Botswana", http://www.avert.org/aids-botswanan.htm last updated Oct. 29, 2009.

* cited by examiner

*Primary Examiner*—Deepak Rao
(74) *Attorney, Agent, or Firm*—Kenneth R. Walton; Sheldon O. Heber

(57) ABSTRACT

Potassium salts of Compound A and methods for their preparation are disclosed, wherein Compound A is of formula:

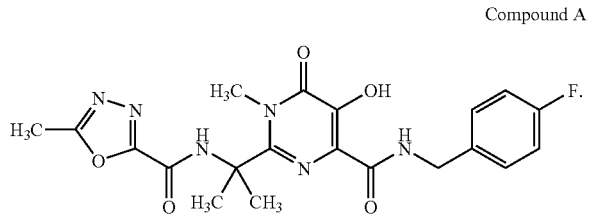

Compound A

Compound A is an HIV integrase inhibitor useful for treating or prophylaxis of HIV infection, for delaying the onset of AIDS, and for treating or prophylaxis of AIDS.

23 Claims, 6 Drawing Sheets

POTASSIUM SALT OF AN HIV INTEGRASE INHIBITOR

This application claims the benefit under 35 U.S.C. 119(e) of U.S. Provisional Application No. 60/633,132, filed Dec. 3, 2004.

FIELD OF THE INVENTION

The present invention is directed to potassium salts of an HIV integrase inhibitor, Compound A as defined below. The present invention is also directed processes for preparing potassium salts of Compound A, pharmaceutical compositions containing the salts, and methods for using the salts.

BACKGROUND OF THE INVENTION

The HIV retrovirus is the causative agent for AIDS. The HIV-1 retrovirus primarily uses the CD4 receptor (a 58 kDa transmembrane protein) to gain entry into cells, through high-affinity interactions between the viral envelope glycoprotein (gp120) and a specific region of the CD4 molecule found in T-lymphocytes and CD4 (+) T-helper cells (Lasky L. A. et al., Cell 1987, 50: 975-985). HIV infection is characterized by an asymptomatic period immediately following infection that is devoid of clinical manifestations in the patient. Progressive HIV-induced destruction of the immune system then leads to increased susceptibility to opportunistic infections, which eventually produces a syndrome called ARC (AIDS-related complex) characterized by symptoms such as persistent generalized lymphadenopathy, fever, and weight loss, followed itself by full blown AIDS.

After entry of the retrovirus into a cell, viral RNA is converted into DNA, which is then integrated into the host cell DNA. Integration of viral DNA is an essential step in the viral life cycle. Integration is believed to be mediated by integrase, a 32 kDa enzyme, in three steps: assembly of a stable nucleoprotein complex with viral DNA sequences; cleavage of two nucleotides from the 3' termini of the linear proviral DNA; and covalent joining of the recessed 3' OH termini of the proviral DNA at a staggered cut made at the host target site. The fourth step in the process, repair synthesis of the resultant gap, may be accomplished by cellular enzymes.

The compound N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide (hereinafter designated as "Compound A") is a potent HIV integrase inhibitor. The structure of Compound A is as follows:

Compound A

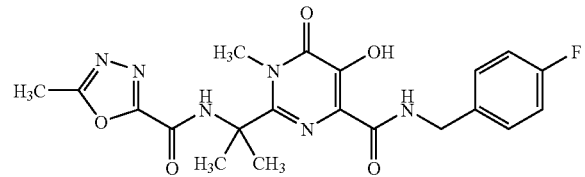

Compound A is disclosed in International Publication No. WO 03/035077.

SUMMARY OF THE INVENTION

The present invention is directed to potassium salts, particularly crystalline salts, of Compound A. The potassium salts of Compound A are significantly more soluble in water compared to the free base, and one crystalline form (identified herein as Form 1) has exhibited improved pharmacokinetics in animal models over the free base. It is further noted that attempts to prepare a crystalline Na salt of Compound A have been unsuccessful, resulting only in amorphous material.

The present invention also includes processes for preparing potassium salts of Compound A and methods of using the Compound A salts for inhibiting HIV integrase, for treating or prophylaxis of HIV infection, and for treating, prophylaxis of, or delaying the onset of AIDS.

The foregoing embodiments and other embodiments, aspects and features of the present invention are either further described in or will be apparent from the ensuing description, examples, and appended claims.

DETAILED DESCRIPTION OF THE INVENTION

Figure 1:
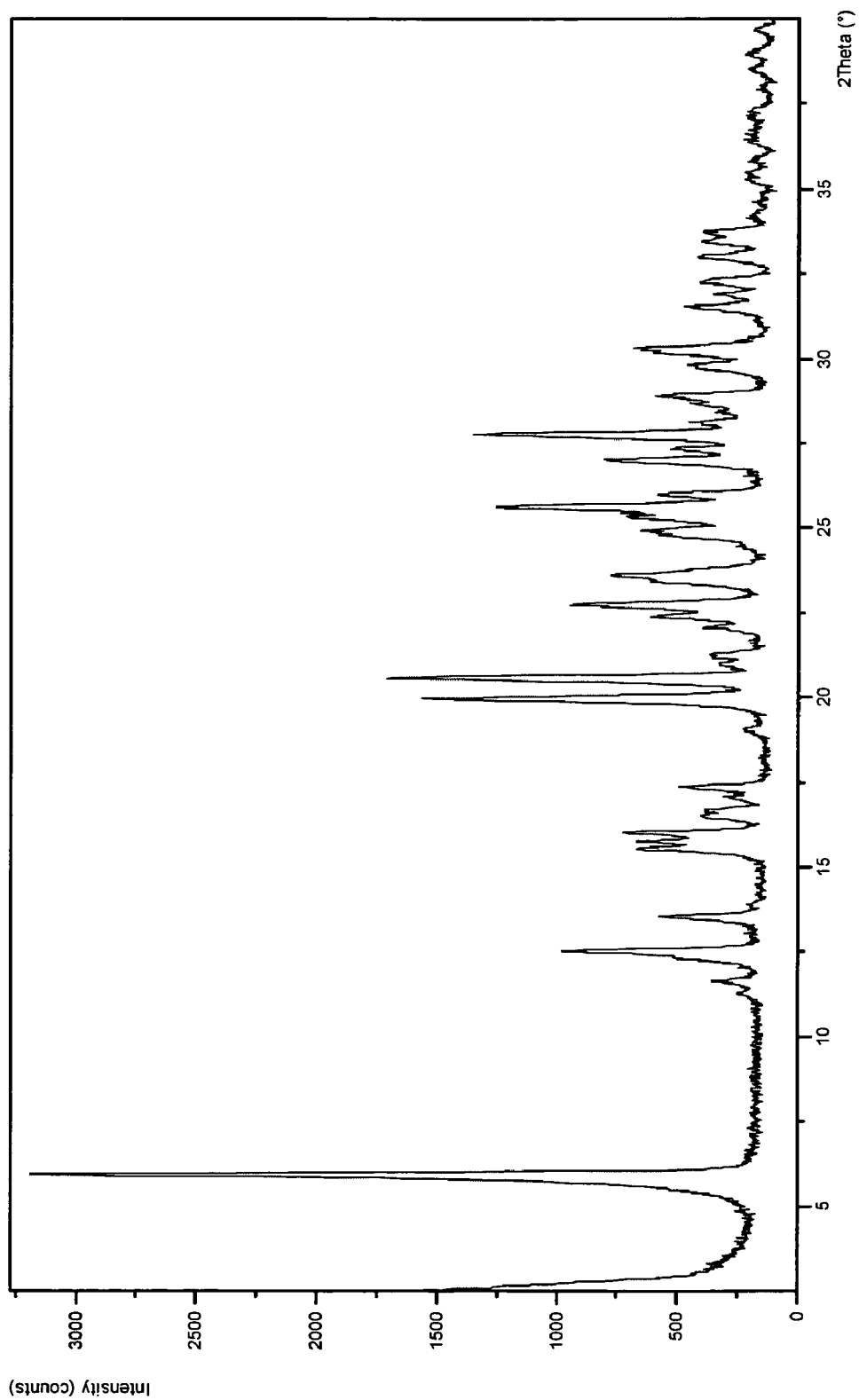
FIG. 1 is the X-ray powder diffraction pattern for the potassium salt of Compound A as prepared in Example 2.

The present invention provides potassium salts of Compound A, pharmaceutical compositions containing the salts and methods of making and using the salts The Compound A potassium salts and pharmaceutical compositions containing the salts are useful for inhibiting HIV integrase, prophylaxis of infection by HIV, treating infection by HIV, delaying the onset of AIDS, prophylaxis of AIDS, and treating AIDS, in adults, children or infants. Delaying the onset of AIDS, prophylaxis of AIDS, treating AIDS, or treating or prophylaxis of infection by HIV is defined as including, but not limited to, treating a wide range of states of HIV infection: AIDS, ARC, both symptomatic and asymptomatic, and actual or potential exposure to HIV. For example, potassium salts of Compound A and pharmaceutical compositions thereof of this invention are useful in treating infection by HIV after suspected past exposure to HIV by, e.g., blood transfusion, exchange of body fluids, bites, accidental needle stick, or exposure to patient blood during surgery. The salts of the invention can also be used in "salvage" therapy; i.e., a potassium salt of Compound A can be used to treat HIV infection, AIDS, or ARC in HIV-positive subjects whose viral load achieved undetectable levels via conventional therapies (e.g., therapies employing known protease inhibitors in combination with one or more known reverse transcriptase inhibitors), and then rebounded due to the emergence of HIV mutants resistant to the known inhibitors.

Compound A is an inhibitor of HIV integrase. Compound A has been tested in an integrase inhibition assay in which strand transfer is catalyzed by recombinant integrase, and has been found to be a potent inhibitor. The strand transfer assay is described in Example 193 of WO 02/30930. Compound A has also been found to be active in an assay for the inhibition of acute HIV infection of T-lymphoid cells conducted in accordance with Vacca et al., *Proc. Natl. Acad. Sci. USA* 1994, 91: 4096-4100.

An embodiment of the present invention is a crystalline potassium salt of Compound A. Another embodiment of the present invention is an anhydrous crystalline potassium salt of Compound A. Still another embodiment of the present invention is an anhydrous crystalline potassium salt of Compound A, which is a Form 1 crystalline potassium salt of Compound A, wherein the Form 1 salt is characterized by an X-ray powder diffraction pattern obtained using copper $K_\alpha$ radiation (i.e., the radiation source is a combination of Cu $K_{\alpha 1}$ and $K_{\alpha 2}$ radiation) which comprises 2Θ values (i.e., reflections at 2Θ values) in degrees of 5.9, 20.0 and 20.6. In an aspect of this embodiment, the Form 1 crystalline potassium salt of Compound A is characterized by an X-ray powder diffraction pattern obtained using copper $K_\alpha$ radiation which comprises 2Θ values in degrees of 5.9, 12.5, 20.0, 20.6 and 25.6. In another aspect of this embodiment, the Form 1 crystalline K salt of Compound A is as originally defined or as defined in the foregoing aspect, and further characterized by a differential scanning calorimetry curve, obtained at a heating rate of 10° C./min in a closed cup under nitrogen, exhibiting a single endotherm with a peak temperature of about 279° C. In still another aspect of this embodiment, the Form 1 crystalline K salt is as originally defined or as defined in either of the preceding aspects, and is further characterized as being a monopotassium salt. The Form 1 crystalline potassium salt of Compound A has exhibited superior oral bioavailability and improved pharmacokinetics (e.g., improved $C_{max}$ and AUC) in rats and dogs relative to Compound A per se.

Another embodiment of the present invention is an anhydrous crystalline potassium salt of Compound A, which is a Form 3 crystalline potassium salt of Compound A, wherein the Form 3 salt is characterized by an X-ray powder diffraction pattern obtained using copper $K_\alpha$ radiation which comprises 2Θ values in degrees of 7.4, 7.8, 12.3, 21.6, and 64.7. In an aspect of this embodiment, the Form 3 crystalline K salt is further characterized by a differential scanning calorimetry curve, obtained at a heating rate of 10° C./min in a closed cup under nitrogen, exhibiting a single endotherm with a peak temperature of about 284° C.

Another embodiment of the present invention is a crystalline potassium salt of Compound A, which is a hydrated crystalline K salt. In still another embodiment, the hydrated crystalline potassium salt is a Form 2 hydrated crystalline potassium salt of Compound A, wherein the Form 2 salt is characterized by an X-ray powder diffraction pattern obtained using copper $K_\alpha$ radiation which comprises 2Θ values in degrees of 7.9, 13.8 and 24.5. In an aspect of this embodiment, the Form 2 crystalline potassium salt of Compound A is characterized by an X-ray powder diffraction pattern obtained using copper $K_\alpha$ radiation which comprises 2Θ values in degrees of 7.9, 13.8, 15.7, 24.5, and 31.5. In another aspect of this embodiment, the Form 2 crystalline K salt of Compound A is as originally defined or as defined in the foregoing aspect, and further characterized by a differential scanning calorimetry curve, obtained at a heating rate of 10° C./min in a closed cup under nitrogen, exhibiting two broad endotherms with peak temperatures of about 146° C. and 239° C. and a third sharp endotherm with a peak temperature of about 276° C.

The present invention includes pharmaceutical compositions comprising a potassium salt of Compound A as originally defined above or as set forth in any of the foregoing embodiments or aspects and a pharmaceutically acceptable carrier.

The present invention also includes pharmaceutical compositions which comprise the product made by combining a potassium salt of Compound A as originally defined above or as set forth in any of the foregoing embodiments or aspects and a pharmaceutically acceptable carrier.

The present invention also includes pharmaceutical combinations of (i) a potassium salt of Compound A as originally defined above or as set forth in any of the foregoing embodiments or aspects and (ii) an anti-HIV agent selected from the group consisting of HIV antiviral agents, immunomodulators, and anti-infective agents; wherein the Compound A K salt and the anti-HIV agent are each employed in an amount that renders the combination effective for inhibiting HIV integrase, for treating or prophylaxis of infection by HIV, or for treating, prophylaxis of, or delaying the onset of AIDS. In one embodiment, the pharmaceutical combinations include a potassium salt of Compound A and an anti-HIV agent which is an antiviral selected from the group consisting of HIV protease inhibitors, non-nucleoside HIV reverse transcriptase inhibitors and nucleoside HIV reverse transcriptase inhibitors.

A pharmaceutical combination of the present invention (i.e., a potassium salt of Compound A in combination with another anti-HIV agent) can be administered separately or together, and when administered separately, the active compounds can be given concurrently or at different times (e.g., alternately). When the active compounds are administered together (either per se or more typically in a pharmaceutical composition), they can both be part of a single composition (e.g., an admixture of the compounds optionally including one or more excipients) or they can be in separate compositions (e.g., encapsulated compositions respectively containing one of the active compounds and optionally one or more excipients) that can be packaged together or separately.

Other embodiments of the present invention include the following:

(a) A method of treating or prophylaxis of HIV infection in a subject in need thereof, which comprises administering to the subject an effective amount of a potassium salt of Compound A.

(b) A method of delaying the onset of AIDS in a subject in need thereof, which comprises administering to the subject an effective amount of a potassium salt of Compound A.

(c) A method of treating or prophylaxis of AIDS in a subject in need thereof, which comprises administering to the subject an effective amount of a potassium salt of Compound A.

(d) A method of inhibiting HIV integrase in a subject in need thereof, which comprises administering to the subject an effective amount of a potassium salt of Compound A.

(e) A method of treating or prophylaxis of HIV infection in a subject in need thereof, which comprises administering to the subject a pharmaceutical composition comprising an effective amount of a potassium salt of Compound A and a pharmaceutically acceptable carrier.

(f) A method of delaying the onset of AIDS in a subject in need thereof, which comprises administering to the subject a pharmaceutical composition comprising an effective amount of a potassium salt of Compound A and a pharmaceutically acceptable carrier.

(g) A method of treating or prophylaxis of AIDS in a subject in need thereof, which comprises administering to the subject a pharmaceutical composition comprising an effective amount of a potassium salt of Compound A and a pharmaceutically acceptable carrier.

(h) A method of inhibiting HIV integrase in a subject in need thereof, which comprises administering to the subject a pharmaceutical composition comprising an effective amount of a potassium salt of Compound A and a pharmaceutically acceptable carrier.

(i) The method of (a) or (b) or (c) or (d), wherein the potassium salt of Compound A is administered in combination with at least one anti-HIV agent selected from the group consisting of AIDS antiviral agents, immunomodulators, and anti-infective agents, wherein the Compound A K salt and the anti-HIV agent are each employed in an amount that renders the combination effective in said method.

(j) The method of (a) or (b) or (c) or (d), wherein the potassium salt of Compound A is administered in combination with at least one antiviral agent selected from the group consisting of HIV protease inhibitors, non-nucleoside HIV reverse transcriptase inhibitors and nucleoside HIV reverse transcriptase inhibitors, wherein the Compound A K salt and the antiviral agent are each employed in an amount that renders the combination effective in said method.

(k) The method of (e) or (f) or (g) or (h), wherein the pharmaceutical composition comprising the Compound A K salt is administered in combination with at least one anti-HIV agent selected from the group consisting of AIDS antiviral agents, immunomodulators, and anti-infective agents, wherein the Compound A K salt and the anti-HIV agent are each employed in an amount that renders the combination effective in said method.

(l) The method of (e) or (f) or (g) or (h), wherein the pharmaceutical composition comprising the Compound A K salt is administered in combination with at least one antiviral agent selected from the group consisting of HIV protease inhibitors, non-nucleoside HIV reverse transcriptase inhibitors and nucleoside HIV reverse transcriptase inhibitors, wherein the Compound A K salt and the antiviral agent are each employed in an amount that renders the combination effective in said method.

Additional embodiments of the invention include the methods set forth in (a)-(l) above, wherein the potassium salt of Compound A employed therein is a Compound A potassium salt as set forth in one of the various embodiments and aspects described above.

The present invention also includes a potassium salt of Compound A of the present invention (i) for use in, (ii) for use as a medicament for, or (iii) for use in the preparation of a medicament for: (a) inhibiting HIV integrase, (b) treating or prophylaxis of infection by HIV, or (c) treating, prophylaxis of, or delaying the onset of AIDS. In these uses, the Compound A K salt of the present invention can optionally be employed in combination with one or more anti-HIV agents selected from HIV antiviral agents, anti-infective agents, and immunomodulators. Embodiments of these uses include the uses as just described wherein the potassium salt of Compound A employed therein is a Compound A potassium salt as set forth in one of the various embodiments and aspects described above.

The present invention includes a process for preparing a crystalline potassium salt of Compound A (alternatively referred to herein as "Process P1" or the "P1 process"), which comprises:

(A1-1) mixing an aqueous solution of a potassium base with a mixture comprising Compound A, water and a first amount of an alcohol to form a basic solution of Compound A and optionally filtering the solution; and (A1-2) seeding the solution formed in Step A1-1 and optionally diluting the seeded solution with a second amount of the alcohol; or (B1-1) seeding a mixture comprising Compound A and a first amount of an organic solvent selected from the group consisting of a halogenated alkane, a dialkyl ether, dialkoxyalkane, a cyclic ether or diether, a trialkylamine, a tertiary amide, an N-alkylpyrrolidone, a dialkyl sulfoxide and an alkanenitrile; and (B1-2) adding an aqueous solution of a potassium base to the seeded mixture of Step B1-1; and (C1) ageing the seeded solution resulting from Step A1-2 or from Step B1-2, to provide the crystalline potassium salt of Compound A.

All of the steps of the P1 process are optionally but preferably conducted with agitation (e.g., stirring).

Compound A has limited solubility in water and in the alcohol (e.g., ethanol) and accordingly Compound A can be difficult to dissolve completely in the alcohol-water mixture. Accordingly, the Compound A-alcohol-water mixture employed in Step A1-1 is typically in the form of a slurry prior to addition of the aqueous base. During Step A1-1, the base reacts with the slurried Compound A converting it to the K salt, which is relatively quite soluble in the alcohol-water mixture, as a result of which the slurry typically is transformed into a relatively clear salt solution. The purpose of the optional filtration in Step A1-1 is to remove any undissolved or precipitated Compound A from the solution and/or to clarify the solution prior to seeding.

Compound A can be employed in Step A1-1 in any amount which will ultimately result in the formation of at least some of the desired crystalline K salt. It is preferred, however, to employ an amount of Compound A which will afford a highly super-saturated solution of the K salt upon completion of the addition of aqueous base in Step A1-1 and prior to seeding, so that the output of crystalline K salt from the process can be maximized.

The purpose of the optional dilution with the alcohol in Step A1-2 is to provide conditions favorable for the crystallization of the K salt; i.e., the K salt is less soluble in the alcohol than in water.

The alcohol employed in Step A1-1 can be any alcohol which under the conditions employed is in the liquid phase, is chemically inert, and will dissolve, suspend, and/or disperse Compound A so as to bring Compound A and the potassium base into contact and permit the crystallization of the desired K salt of Compound A. The alcohol is typically one in which Compound A has a higher solubility than the K salt of Compound A, so as to provide conditions favorable for the crystallization of the K salt of Compound A. Alcohols suitable for use in Step A1-1 include alkyl alcohols and cycloalkyl alcohols, such as $C_{1-6}$ alkyl alcohols and $C_{4-6}$ cycloalkyl alcohols. Suitable alcohols include, for example, methanol, ethanol, propanol, isopropanol, cyclobutanol, and cyclopentanol. In one embodiment, the alcohol is a $C_{1-4}$ alkyl alcohol. In another embodiment, the alcohol is methanol or ethanol. A preferred alcohol for use in Step A1-1 is ethanol.

The organic solvent employed in Step B1-1 can be any halogenated alkane, dialkyl ether, dialkoxyalkane, cyclic ether or diether, trialkylamine, tertiary amide, N-alkylpyrrolidone, dialkylsulfoxide, or alkanenitrile which under the conditions employed is in the liquid phase, is chemically inert, and will dissolve, suspend, and/or disperse Compound A so as to bring Compound A and the potassium base into contact and permit the crystallization of the desired K salt of Compound A. The physical state of the organic solvent-Compound A mixture prior to seeding will depend upon such factors as the choice of solvent, the amount of Compound A employed, and temperature. The mixture can be, for example, a solution in which Compound A is completely dissolved in the organic solvent or a slurry in which some portion (from minor to major) of Compound A remains undissolved. Some solvents (e.g., DMSO, acetonitrile, NMP and DMF) typically form solutions with Compound A (i.e., dissolve essentially all of the Compound A) for the concentrations of Compound A and under the conditions typically employed in Step B1-1. Undissolved Compound A in the B1-1 mixture will typically go into solution during addition of the aqueous base in Step B1-2 and subsequently either crystallize or remain in solution as the K salt.

The organic solvent in Step B1-1 is also typically one in which Compound A has a higher solubility than does the K salt of Compound A, so as to afford conditions favorable for the crystallization of the K salt of Compound A.

Representative examples of solvents suitable for use in Step B1-1 include carbon tetrachloride, chloroform, methylene chloride, 1,2-dichloroethane, 1,1,2-trichloroethane, 1,1,2,2-tetrachloroethane, ethyl ether, MTBE, THF, dioxane, 1,2-dimethoxyethane, triethylamine, tri-n-propylamine, diethylisopropylamine, diisopropylethylamine, DMF, DMAC, N-methylpyrrolidone, N-ethylpyrrolidone, DMSO, acetonitrile, and propionitrile.

An embodiment of Process P1 is the process as originally set forth above, wherein the organic solvent employed in Step B1-1 is a $C_{1-8}$ linear or branched halogenated alkane, a dialkyl ether wherein each alkyl is independently a $C_{1-4}$ alkyl, a $C_{1-4}$ linear or branched alkane substituted with two —O—$C_{1-4}$ alkyl groups (which are the same or different), a $C_4$-$C_6$ cyclic ether or diether, a tri-($C_{1-4}$ alkyl)amine, a N,N-di-($C_{1-4}$ alkyl)-$C_{1-4}$ alkylamide, a N—($C_{1-4}$ alkyl)pyrrolidone, a di-($C_{1-4}$ alkyl)sulfoxide, or a $C_2$-$C_4$ alkanenitrile.

In another embodiment, the organic solvent employed in Step B1-1 is acetonitrile, propionitrile, THF, DMF, DMAC, N-methylpyrrolidone, or N-ethylpyrrolidone. In a preferred embodiment, the solvent is acetonitrile or NMP.

The potassium base employed in Step A1-1 or Step B1-2 suitably comprises potassium hydroxide, potassium carbonate, potassium bicarbonate, or potassium alkoxide. The term "potassium alkoxide" refers to a potassium salt of an alkyl alcohol. The potassium alkoxide is suitably the salt of a $C_{1-6}$ alkyl alcohol (i.e., KOR where R is $C_{1-6}$ alkyl), and is typically the salt of a $C_{1-4}$ alkyl alcohol. Suitable potassium alkoxides include, for example, potassium methoxide, potassium ethoxide, potassium propoxide, and potassium isopropoxide. An embodiment of the P1 process is the process as originally set forth above or as set forth in a preceding embodiment, wherein, when a potassium alkoxide is employed in Step A1-1, the alcohol has the same alkyl group as the alkoxide base; i.e., MeOH is employed with KOMe, EtOH is employed with KOEt, i-PrOH is employed with potassium isopropoxide, and so forth.

Another embodiment of Process P1 is the process as originally set forth above or as set forth in a preceding embodiment, wherein the potassium base employed in Step A1-1 or Step B1-2 comprises KOH, KOMe, and KOEt. In an aspect of this embodiment, the potassium base is KOH.

The potassium base (e.g., KOH) can be employed in any proportion with respect to Compound A which results in the formation of at least some of the desired potassium salt. The base can suitably be added in an amount in a range of from about 0.1 to about 3 equivalents per equivalent of Compound A. The base is typically added in a proportion which, under the reaction conditions employed (e.g., temperature, degree of agitation, etc.), will permit conversion of at least a major portion (i.e., more than 50%) of Compound A to the desired salt. The use of excess amounts of base can lead to the formation of hydrolysis products, whereas the use of sub-equivalent amounts of base can unduly restrict the level of conversion resulting in excessive amounts of unreacted Compound A. Accordingly, the base is typically added in an amount in a range of from about 0.5 to about 1.1 equivalents per equivalent of Compound A, and is more typically added in an amount in a range of from about 0.9 to about 1.0 equivalent (e.g., from about 0.90 to about 0.98 equivalent) per equivalent of Compound A.

Any amount of seed crystal can be employed in Step A1-2 or Step B1-2, which will induce or assist in the crystallization of the desired crystalline form of Compound A K salt. Relatively very small amounts of crystal are typically not employed since they can be minimally effective in inducing or assisting crystallization. On the other hand, very large amounts of crystal are typically not employed, because it is wasteful of material, exceeding the amount necessary for effecting crystallization. Accordingly, the seed crystals are suitably employed in an amount in a range of from about 0.2 to about 10 wt. % (e.g., from about 0.5 to about 10 wt. %) based on the weight of Compound A (e.g., 10 wt. % means 10 g of seed is employed per 100 g of Compound A), and is typically employed in an amount in a range of from about 1 to about 5 wt. % based on the weight of Compound A.

Steps A1-1 and A1-2 or Steps B1-1 and B1-2 can be conducted over a wide temperature range, wherein the temperature for Step A1-1 or Step B1-2 is such that Compound A is soluble in the reaction medium (i.e., a base-containing seeded solution of a suitable organic solvent as set forth above and water) and the crystalline salt of Compound A is at least partially insoluble in the medium. Each step is suitably conducted at a temperature in a range of from about 0 to about 60° C., is typically conducted at a temperature in a range of from about 20 to about 50° C., and is more typically conducted at a temperature in a range of from about 20 to about 30° C. (e.g., from about 20 to about 25° C.).

The ageing in Step C1 can be conducted at any temperature which leads to the formation of the desired crystalline form of Compound A K salt. Step C1 is suitably conducted at a temperature in a range of from about 0 to about 60° C., is typically conducted at a temperature in a range of from about 0 to about 50° C. (e.g., from about 15 to about 50° C.), and is more typically conducted at a temperature in a range of from about 0 to about 30° C. (e.g., from about 20 to about 30° C.).

An embodiment of the P1 process is the process as originally set forth above or as set forth in a preceding embodiment, wherein Steps A1-1, A1-2 and C1 or Steps B1-1, B1-2 and C1 are all conducted in the same temperature range. In an aspect of this embodiment, each of the steps is conducted at a temperature in a range of from about 20 to about 30° C. (e.g., from about 20 to about 25° C.).

Another embodiment of the P1 process is the process as originally set forth above or as set forth in a preceding embodiment, wherein Steps A1-1 and A1-2 or Steps B1-1 and B1-2 are each conducted in the same temperature range, but Step C1 is conducted at a lower temperature. In an aspect of this embodiment, Steps A1-1 and A1-2 or Steps B1-1 and B1-2 are each conducted at a temperature in a range of from about 20 to about 30° C. (e.g., from about 20 to about 25° C.), and Step C1 is conducted at a temperature in a range of from about 0 to about 20° C. (e.g., from about 0 to about 10° C.). In another aspect of this embodiment, Steps A1-1 and A1-2 or Steps B1-1 and B1-2 are each conducted at a temperature in a range of from about 20 to about 30° C. (e.g., from about 20 to about 25° C.), and Step C1 is conducted at a temperature in a range of from about 0 to about 10° C. (e.g., from about 0 to about 5° C.).

The ageing time can vary over a wide range depending upon, inter alia, the ageing temperature, the choice of solvent, the choice of base, and the relative amounts and concentrations of Compound A, base, and crystal seed. The ageing is typically conducted for a time sufficient to obtain 50% or more (and preferably 90% or more) of the theoretical yield of K salt from the mother liquor. In any event, the ageing time is typically in a range of from about 0.1 to about 24 hours, and is more typically in a range of from about 0.5 to about 12 hours. It is typically desirable to avoid relatively long ageing times (e.g., more than about 12 hours), since it has been observed that the level of impurities being incorporated into the crystalline product can increase with increasing ageing time.

The proportion of water to alcohol employed in Step A1-1 can vary over a wide range. On the other hand, the potassium salt of Compound A is comparatively quite soluble in water, and thus it can be desirable to limit the proportion of water employed in order to increase crystallization yield from the mother liquor. The volume to volume ratio of alcohol to water can suitably be in a range of from about 80:20 to about 20:80, is typically in a range of from about 70:30 to about 30:70, and is more typically in a range of from about 60:40 to about 40:60 (e.g., from about 55:45 to about 45:55).

In Step A1-2, the seeded solution can be diluted with a further amount of the alcohol. As noted earlier, the Compound A K salt is less soluble in the alcohol than in water, and thus dilution with the alcohol tends to provide conditions favorable for the crystallization of the K salt. The volume to volume ratio of solvent alcohol to water in the diluted, seeded solution can suitably be at least about 60:40, is typically at least about 80:20 (e.g., from about 95:5 to about 80:20), and is more typically at least about 90:10 (e.g., from about 95:5 to about 90:10).

The organic solvent and water can be present in Step B1-2 in any proportion with respect to each other that results in the formation of at least some crystalline K salt of Compound A. As noted above, Compound A has a higher solubility in the organic solvent than does the Compound A K salt, and thus increasing the proportion of organic solvent tends to favor crystallization of the K salt. On the other hand, the Compound A K salt is typically more soluble in water than in the organic solvent, and thus it is desirable to limit the amount of water introduced into the system via addition of the aqueous base, in order to minimize the amount of salt left behind in the mother liquor during crystallization. The volume to volume ratio of organic solvent to water in the Step B1-2 solution can suitably be at least about 70:30, is typically at least about 80:20 (e.g., from about 95:5 to about 80:20), and is more typically at least about 90:10 (e.g., from about 95:5 to about 90:10).

Other embodiments of the P1 process include the process as originally set forth and as set forth in each of the preceding embodiments, wherein each of the processes further comprises:

(D1) recovering the crystalline K salt of Compound A from the aged solution. In an aspect of this embodiment, the crystalline K salt is recovered by filtration to obtain a crystalline cake, optionally washing the cake with another organic solvent which is the same or different as the alcohol employed in Step A1-1 or the organic solvent employed in Step B1-1, and drying.

Another embodiment of the P1 process is the process which comprises:

(A1-1) mixing an aqueous solution of KOH with a mixture comprising Compound A, water and a first amount of ethanol to form a basic solution of Compound A and optionally filtering the solution;

(A1-2) seeding the solution formed in Step A1-1 and diluting the seeded solution with a second amount of ethanol to obtain a diluted, seeded solution; and (C1) ageing the diluted, seeded solution of Step A1-2, to provide the crystalline K salt of Compound A.

Aspects of the preceding embodiment include the process as just described, incorporating one or more of the following features (i) to (viii):

(i) Step A1-1 is conducted at a temperature in a range of from about 20 to about 50° C. (e.g., from about 20 to about 30° C.);

(ii) Step A1-2 is conducted at a temperature in a range of from about 20 to about 50° C. (e.g., from about 20 to about 30° C.);

(iii) Step C1 is conducted at a temperature in a range of from about 0 to about 30° C. (e.g., from about 0 to about 20° C., or from about 0 to about 10° C.);

(iv) in Step A1-1, the basic solution has a volume to volume ratio of ethanol to water in a range of from about 70:30 to about 30:70;

(v) in Step A1-2, the diluted, seeded solution has a volume to volume ratio of ethanol to water of at least about 80:20;

(vi) seed crystals are employed in an amount in a range of from about 0.2 to about 5 wt. % (or from about 1 to about 5 wt. %) based upon the total weight of Compound A;

(vii) KOH is employed in an amount in a range of from about 0.9 to about 1.1 equivalents (e.g., from about 0.9 to about 0.98 equivalent) per equivalent of Compound A; and (viii) the process further comprises step D1, which is recovering the crystalline K salt of Compound A (e.g., by separating the crystalline K salt from the aged solution by filtration to obtain a crystalline cake, optionally washing the cake with a third amount of ethanol, and drying).

Still another embodiment of the P1 process is the process which comprises:

(B1-1) seeding a solution comprising Compound A and acetonitrile;

(B1-2) adding an aqueous solution of KOH to the seeded solution formed in Step B1-1; and (C1) ageing the solution of Step B1-2, to provide the crystalline K salt of Compound A.

Aspects of the preceding embodiment include the process as just described, incorporating one or more of the following features (i) to (vii):

(i) Step B1-1 is conducted at a temperature in a range of from about 20 to about 50° C. (e.g., from about 20 to about 30° C.);

(ii) Step B1-2 is conducted at a temperature in a range of from about 20 to about 50° C. (e.g., from about 20 to about 30° C.);

(iii) Step C1 is conducted at a temperature in a range of from about 20 to about 50° C. (e.g., from about 20 to about 30° C.);

(iv) the seeded solution obtained in Step B1-2 has a volume to volume ratio of acetonitrile to water of at least about 90:10;

(v) seed crystals are employed in an amount in a range of from about 0.2 to about 5 wt. % (or from about 1 to about 5 wt. %) based upon the total weight of Compound A;

(vi) KOH is employed in an amount in a range of from about 0.9 to about 1.1 equivalents (e.g., from about 0.9 to about 0.98 equivalent) per equivalent of Compound A; and (vii) the process further comprises Step D1, which is recovering the crystalline K salt of Compound A (e.g., by separating the crystalline K salt from the aged solution by filtration to obtain a crystalline cake, washing the cake with acetonitrile, and drying).

Additional embodiments of the P1 process of the invention include the process as originally set forth and as set forth in each of the preceding embodiments, wherein crystal seed employed in the process comprises Form 1 crystalline potassium salt of Compound A and the crystalline salt resulting from the process comprises Form 1 crystalline potassium salt of Compound A.

The seeding step set forth above in Process P1 is optional in the sense that crystalline Compound A K salt can be obtained without seeding. Seeding is preferred, however, as a means of inducing or assisting crystallization generally and of preparing specific crystalline forms (e.g., Form 1) particularly.

The present invention includes a process for preparing a crystalline potassium salt of Compound A (alternatively referred to herein as "Process P2" or the "P2 process"), which comprises:

(A2) adding:

(i) a feed solution comprising Compound A and (a) a first amount of a first solvent selected from the group consisting of a dialkyl ketone, a dialkyl ether, dialkoxy alkane, a cyclic ether or diether, a trialkylamine, a tertiary amide, an N-alkylpyrrolidone, a dialkylsulfoxide, and an alkanenitrile and (b) a first amount of a second solvent selected from the group consisting of an alcohol, an alkane, an alkyl ester of an alkylcarboxylic acid, and an aromatic hydrocarbon, and (ii) a feed mixture comprising a potassium alkoxide base and a second amount of the second solvent, to a crystallizer containing seed crystals slurried in a solvent mixture comprising a second amount of the first solvent and a third amount of the second solvent to obtain a crystallization mixture; wherein at least a substantial portion of the feed solution and the feed mixture are added to the crystallizer concurrently; and (B2) ageing the crystallization mixture obtained in Step A2, to provide the crystalline potassium salt of Compound A.

As used herein, the term "crystallizer" means a reaction vessel in which the crystallization of the K salt of Compound A is conducted.

At least a substantial portion of the feed solution and the feed mixture (i.e., for each feed an amount independently ranging from at least 60% to 100%) are added concurrently (i.e., at the same time) to the crystallizer in Step A2. Thus, for example, in Process P2 at least about 60% (e.g., from about 60% to about 99%), or at least about 80% (e.g., from about 80% to about 99%), or at least about 90% (e.g., from about 90% to about 99%), or 100% of the feed solution and the feed mixture can be added concurrently to the crystallizer in Step A2. It is understood, however, that minor portions of either or both feeds can be added to the crystallizer nonconcurrently, including but not limited to non-concurrent additions of portions of one or both feeds (e.g., sequential addition) before or after a single concurrent addition or between two separate concurrent additions. In one embodiment, the two feeds are added concurrently until all of the feed solution (containing Compound A) and a substantial portion of the feed mixture (containing the base) are added to the crystallizer, followed by addition of the remaining amount of the feed mixture.

The addition in Step A2 is suitably conducted with agitation in order to prevent or minimize locally high concentrations of base with respect to Compound A, which can lead to the formation of hydrolysis products. Indeed the entire process (Steps A2 and B2) is typically conducted with agitation (e.g., stirring).

In the feed solution in Step A2, Compound A is completely dissolved in the medium formed by the first and second solvents. On the other hand, the feed mixture in Step A2 can be a solution in which the alkoxide base is completely dissolved in the second solvent, or it can be a slurry in which the base is only partially dissolved in the second solvent. The physical state of the feed mixture will depend upon such factors as the choice and relative amounts of solvent and base and the temperature. The feed mixture is preferably a solution, such as a solution of the alkoxide in an alcohol.

An important function of the first and second solvents is as the medium for Compound A in the feed solution, such that Compound A is completely dissolved therein and readily available for contact with the alkoxide base. An important function of the second solvent is as the medium for the alkoxide base in the feed mixture, such that it dissolves, suspends, and/or disperses the alkoxide so as to permit its contact and reaction With Compound A. In addition, the first and second solvents in Process P2 together provide a solvent system in which Compound A has relatively high solubility and the desired K salt of Compound A has relatively low solubility, so as to afford conditions favorable for the crystallization of the K salt. All of the foregoing factors are to be taken into account in selecting the relative proportions in which a particular pair of first and second solvents are employed in the feed solution, the crystal slurry, and the ageing step. For example, Compound A has been found to be more soluble in MeCN (first solvent)-EtOH (second solvent) mixtures for solvent volume ratios in a range of from about 20:80 to about 80:20 compared to its solubility in either MeCN or EtOH alone, whereas the K salt has a comparatively very low solubility over the range of volume ratios. Accordingly, when MeCN and EtOH are selected as the first and second solvents in the P2 process, the solvents are typically employed both to provide a suitable feed solution, feed mixture, and crystal slurry and to afford a final solvent volume ratio (i.e., the volume ratio of the first and second solvents upon completion of charging the feed solution and the feed mixture to the crystallizer) in the 20:80 to 80:20 range.

Compound A can be employed in the feed solution at any concentration which will ultimately result in the formation of at least some of the desired crystalline potassium salt, but is typically employed in the feed solution at a concentration at or close to that which provides a saturated feed solution which in turn can afford a highly super-saturated K salt solution, in order to maximize the output of crystallized K salt from the process.

The first solvent can be any dialkyl ketone, dialkyl ether, dialkoxy alkane, cyclic ether or diether, trialkylamine, tertiary amide, N-alkylpyrrolidone, dialkylsulfoxide, or alkanenitrile which under the conditions employed is in the liquid phase, is chemically inert, and can, either by itself or in combination with a suitable amount of the second solvent, dissolve all of Compound A employed in the feed solution. Compound A is typically more soluble in the first solvent per se than in the second solvent per se, and the first solvent is typically primarily responsible for dissolution of Compound A in the feed solution.

A class of substances suitable for use as the first solvent consists of any substance selected from the group consisting of a di-($C_{1-4}$ alkyl) ketone, a dialkyl ether wherein each alkyl is independently a $C_{1-4}$ alkyl, a $C_{1-4}$ linear or branched alkane substituted with two —O—$C_{1-4}$ alkyl groups (which are the same or different), a $C_4$-$C_6$ cyclic ether or diether, a tri-($C_{1-4}$)alkylamine, a N,N-di-($C_{1-4}$ alkyl)-$C_{1-4}$ alkylamide, an N—($C_{1-4}$ alkyl)pyrrolidone, a di-($C_{1-4}$ alkyl)sulfoxide, and a $C_2$-4 alkanenitrile.

Substances suitable for use as the first solvent in Step A2 include, for example, acetone, ethyl ether, MTBE, THF, dioxane, 1,2-dimethoxyethane, triethylamine, tri-n-propylamine, diethylisopropylamine, diisopropylethylamine, DMF, DMAC, N-methylpyrrolidone, N-ethylpyrrolidone, DMSO, acetonitrile, and propionitrile. In a preferred embodiment, the first solvent is acetone, THF, DMF, NMP, DMSO, or acetonitrile.

A class of substances suitable for use as the second solvent consists of any substance which is a $C_{1-4}$ alkyl alcohol, a $C_{4-8}$ linear or branched alkane, a $C_{1-4}$ alkyl ester of a $C_{1-4}$ alkylcarboxylic acid, or a mono- or di- or tri-$C_{1-4}$ alkyl benzene.

Substances suitable for use as the second solvent in Step A2 include, for example, methanol, ethanol, isopropanol, hexane, heptane, ethyl acetate, isopropyl acetate, toluene, o-xylene, m-xylene, p-xylene, and ethylbenzene. In a preferred embodiment, the second solvent is ethanol, heptane, ethyl acetate, or toluene.

Combinations of first solvent and second solvent that are particularly suitable for use in Step A2 include acetonitrile/ethanol and NMP/ethanol.

Potassium alkoxides suitable for use in Step A2 are the same as those described earlier in the discussion of the P1 process. An embodiment of the P2 process is the P2 process as originally set forth above or as set forth in a preceding embodiment, wherein the potassium alkoxide employed in Step A2 is the potassium salt of a $C_{1-4}$ alkyl alcohol. In a preferred embodiment of the P2 process, the potassium alkoxide is KOMe or KOEt, and is especially KOEt. In another preferred embodiment, the second solvent is a $C_{1-4}$ alkyl alcohol and the base is the corresponding potassium alkoxide; i.e., the following combinations are employed in the process: MeOH+KOMe, EtOH+KOEt, i-PrOH+KOi-Pr, and so forth.

The potassium alkoxide base can be employed in any proportion with respect to Compound A which results in the formation of at least some of the desired crystalline potassium salt, but the base is typically employed in an amount that will permit conversion of at least a major portion of Compound A to the crystalline K salt. Amounts of potassium alkoxide suitable for use in the instant process are the same as those set forth above with respect to use of potassium base in the P1 process. As in the P1 process, the use of excessive amounts of potassium alkoxide can lead to the formation of hydrolysis products such as the following which are believed to form when KOEt is employed as the base:

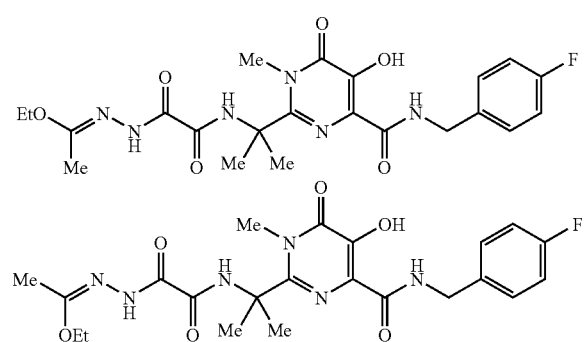

In further analogy with the P1 process, the use of sub-equivalent amounts of base can result in a low conversion to crystalline K salt.

Any amount of seed crystal can be employed in Step A2 which will induce or assist in the crystallization of the desired crystalline form of Compound A K salt. Similar considerations as set forth above with respect to the amount of crystal seed employed in the P1 process apply here. The seed crystal can suitably be employed in Step A2 in an amount in a range of from about 1 to about 30 wt. % based on the weight of Compound A, is typically employed in an amount in a range of from about 10 to about 25 wt. %, and is more typically employed in an amount in a range of from about 15 to about 25 wt. % (e.g., about 20 wt. %).

Steps A2 and B2 can each be conducted over a wide temperature range. Step A2 can suitably be conducted at a temperature in a range of from about 0 to about 60° C., is typically conducted at a temperature in a range of from about 20 to about 50° C., and is more typically conducted at a temperature in a range of from about 30 to about 50° C. (e.g., from about 40 to about 45° C.). Step B2 can suitably be conducted at a temperature in a range of from about 0 to about 60° C., is typically conducted at a temperature in a range of from about 15 to about 50° C., and is more typically conducted at a temperature in a range of from about 20 to about 40° C. In a preferred embodiment, the ageing in Step B2 is initially conducted at a temperature in a range of from about 30 to about 40° C. and then at a temperature in a range of from about 20 to about 30° C. until completion/termination of the ageing step, wherein the drop in temperature typically results in a decrease in the solubility of the Compound A K salt and concomitantly in an increase in the yield of the crystalline K salt.

The rates of addition of the feed solution and the feed mixture to the crystallizer employed during concurrent addition can be the same or different and each can vary over a wide range, with the proviso that substantial portions of the feed solution and feed mixture are charged to the crystallizer during the concurrent addition. In a preferred embodiment, the rates of addition are controlled during concurrent addition such that the ratio of equivalents of alkoxide base to equivalents of Compound A is a constant, wherein the rates of addition required to maintain the constant ratio (alternatively referred to as a "fixed ratio") will depend upon the concentration of Compound A in the feed solution and the concentration of base in the feed mixture. In another preferred embodiment, the feed solution and the feed mixture are concurrently added to the crystallizer at rates which provide a constant ratio of equivalents of alkoxide base to equivalents of Compound A until all of the feed solution (containing Compound A) has been added, and then the remaining feed mixture (containing alkoxide base) is added.

When a constant ratio of equivalents of alkoxide base to equivalents of Compound A is employed during concurrent addition, the volume ratio of the first solvent to the second solvent is also constant, which can provide an advantage over the P1 process. In the P1 process described above, a relatively high level of uncontrolled nucleation and agglomeration of the K salt can occur. A significant amount of occlusion of the organic solvent in the crystalline K salt can also occur. The uncontrolled nucleation, the agglomeration, and the occlusion are all believed to be due in part to the constantly changing solvent composition (and thus a constantly changing super-saturation profile) during addition Step A1-1 or B1-2 of process P1; i.e., there is a constantly increasing amount of water as the aqueous potassium base is added to the Compound A-containing medium. The P2 process can mitigate the uncontrolled nucleation and agglomeration by maintaining a constant solvent composition during the concurrent addition, and thereby can provide a crystalline product consisting predominantly of primary crystals instead of agglomerates.

It is further preferred that the final solvent volume ratio be the same as the volume ratio of the first solvent to the second solvent in the crystal slurry prior to addition of the two feeds (i.e., the "crystal slurry solvent volume ratio"). This helps to control nucleation and avoid agglomeration, and it also facilitates use of a portion of the crystalline product resulting from the ageing step as a crystal slurry in a subsequent run (i.e., facilitates use of the crystal as a "heel") in that the slurry will have the appropriate solvent volume ratio for use in Step A2.

Unless expressly stated to the contrary, the solvent volume ratios refer herein to ratios of the volumetric amount of each solvent measured at a temperature of about 25° C. prior to being mixed together. Thus, for example, a crystal slurry solvent volume ratio of 80:20 for solvent X to solvent Y means that 80 parts by volume of solvent X (e.g., 80 mL of X) and 20 parts by volume of solvent Y (e.g., 20 mL of Y) are separately measured out at about 25° C., and the measured portions of the solvents are then employed to prepare the seed crystal slurry.

Embodiments of the P2 process include the process as originally set forth above incorporating one or more of the following features (i) to (viii):

(i) in Step A2 the potassium alkoxide base is employed in an amount in a range of from about 0.5 to about 1.1 equivalents (or from about 0.9 to about 1.1 equivalents, or from about 0.90 to about 1.0 equivalent) per equivalent of Compound A;

(ii) Step A2 is conducted at a temperature in a range of from about 0 to about 60° C. (or from about 20 to about 50° C., or from about 30 to about 50° C., or from about 40 to about 45° C.);

(iii) in Step A2 the feed solution and the feed mixture are concurrently added to the crystallizer until all of the feed solution and a substantial portion of the feed mixture are added, followed by addition of the remaining feed mixture;

(iv) the seed crystals are employed in Step A2 in an amount in a range of from about 1 to about 30 wt. % (or from about 10 to about 25 wt. %, or from about 15 to about 25 wt. %);

(v) Step B2 is conducted at a temperature in a range of from about 0 to about 60° C. (or from about 15 to about 50° C., or from about 20 to about 40° C., or initially from about 30 to about 40° C. and then from about 20 to about 30° C. until completion/termination of the ageing step);

(vi) the crystallization mixture in Step A2 has a final solvent volume ratio of first solvent to second solvent in a range of from about 80:20 to about 20:80 (or from about 60:40 to about 20:80);

(vii) prior to addition of the feed solution and the feed mixture in Step A2, the crystal slurry has a crystal slurry solvent volume ratio of first solvent to second solvent of from about 80:20 to about 20:80 (or from about 60:40 to about 20:80); and (viii) the crystal slurry solvent volume ratio is about the same as the final solvent volume ratio.

Other embodiments of the P2 process include the processes as described in any of the immediately preceding embodiments (i.e., the processes incorporating one or more of features i to viii), wherein:

the first solvent is acetone, ethyl ether, MTBE, THF, dioxane, 1,2-dimethoxyethane, triethylamine, tri-n-propylamine, diethylisopropylamine, diisopropylethylamine, DMF, DMAC, N-methylpyrrolidone, N-ethylpyrrolidone, DMSO, acetonitrile, or propionitrile;

the second solvent is methanol, ethanol, isopropanol, hexane, heptane, ethyl acetate, isopropyl acetate, toluene, o-xylene, m-xylene, p-xylene, or ethylbenzene; and the potassium alkoxide is KOMe or KOEt.

In an aspect of each of these embodiments, the first solvent is acetone, THF, DMF, NMP, DMSO, or acetonitrile; the second solvent is EtOH, heptane, EtOAc, or toluene; and the potassium alkoxide is KOEt.

Still other embodiments of the P2 process include the processes as set forth in the two immediately preceding sets of embodiments, wherein during the concurrent addition of the feed solution and the feed mixture, the feeds are added to the crystallizer at rates which provide a constant ratio of equivalents of alkoxide base to equivalents of Compound A.

Other embodiments of the P2 process include the process as originally set forth and as set forth in each of the preceding embodiments, wherein each of the processes further comprises:

(C2) recovering the crystalline K salt of Compound A from the aged mixture. In an aspect of this embodiment, the crystalline K salt is recovered by filtration to obtain a crystalline cake, optionally washing the cake with a third amount of the first solvent, the second solvent, or a combination thereof, and drying.

Still another embodiment of the P2 process is the process which comprises:

(A2) adding a feed solution comprising Compound A, a first amount of acetonitrile, and a first amount of ethanol and a feed mixture which is a solution comprising potassium ethoxide and a second amount of ethanol to a crystallizer containing seed crystals slurried in a solvent mixture comprising a second amount of acetonitrile and a third amount of ethanol to obtain a crystallization mixture; wherein at least a substantial portion of the first and second solutions are added to the crystallizer concurrently; and (B2) ageing the crystallization mixture obtained in Step A2, to provide the crystalline potassium salt of Compound A.

Aspects of the preceding embodiment include the process as just described, incorporating one or more of the following features (i) to (x):

(i) in Step A2 potassium ethoxide is employed in an amount in a range of from about 0.5 to about 1.1 equivalents (or from about 0.9 to about 1.1 equivalents, or from about 0.90 to about 1.0 equivalent) per equivalent of Compound A;

(ii) Step A2 is conducted at a temperature in a range of from about 0 to about 60° C. (or from about 20 to about 50° C., or from about 30 to about 50° C., or from about 40 to about 45° C.);

(iii) in Step A2 the feed solution and the feed mixture are concurrently added to the crystallizer until all of the feed solution and a substantial portion of the feed mixture are added, followed by addition of the remaining feed mixture;

(iv) Step B2 is conducted at a temperature in a range of from about 0 to about 60° C. (or from about 15 to about 50° C., or from about 20 to about 40° C., or from about 30 to about 40° C. and then from about 20 to about 30° C. until completion);

(v) seed crystals are employed in an amount in a range of from about 1 to about 30 wt. % (or from about 10 to about 25 wt. %, or from about 15 to about 25 wt. %);

(vi) the crystallization mixture in Step A2 has a final solvent volume ratio of acetonitrile to ethanol in a range of from about 80:20 to about 20:80 (or from about 60:40 to about 20:80, or from about 50:50 to about 20:80, or from about 30:70 to about 20:80);

(vii) prior to addition of the feed solution and the feed mixture in Step A2, the crystal slurry has a crystal slurry solvent volume ratio of acetonitrile to ethanol that is about the same as the final solvent volume ratio;

(viii) during the concurrent addition of the feed solution and the feed mixture, the feeds are added to the crystallizer at rates which provide a constant ratio (i.e., fixed ratio) of equivalents of potassium ethoxide to equivalents of Compound A;

(ix) the time of addition of the feed solution and the feed mixture in Step A2 is in a range of from about 0.5 to about 24 hours (or from about 8 to about 16 hours—e.g., about 12 hours); and (x) the process further comprises Step C2, which is recovering the crystalline K salt of Compound A (e.g., by separating the crystalline K salt from the aged solution by filtration to obtain a crystalline cake, optionally washing the cake with ethanol, and drying).

Additional embodiments of the P2 process of the invention include the process as originally set forth and as set forth in each of the preceding embodiments, wherein crystal seed employed in the process comprises Form 1 crystalline potassium salt of Compound A and the crystalline salt resulting from the process comprises Form 1 crystalline potassium salt of Compound A.

The seeding step set forth above in Process P2 is optional in the sense that crystalline Compound A K salt can be obtained without seeding. Seeding is preferred, however, as a means of inducing or assisting crystallization generally and of preparing specific crystalline forms (e.g., Form 1) particularly.

The present invention includes a process for preparing a crystalline potassium salt of Compound A (alternatively referred to herein as "Process P3" or the "P3 process"), which comprises:

(A3) adding (i) a first solution comprising Compound A and a first amount of a water-dissolving organic solvent selected from the group consisting of a dialkyl ketone, a dialkyl ether, dialkoxy alkane, a cyclic ether or diether, a trialkylamine, a tertiary amide, an N-alkylpyrrolidone, a dialkylsulfoxide, and an alkanenitrile, and (ii) a second solution comprising KOH and a first amount of water, to a crystallizer containing seed crystals slurried in a mixture comprising a second amount of the organic solvent and a second amount of water; wherein at least a substantial portion of the first and second solutions are added to the crystallizer concurrently; and (B3) ageing the crystallization mixture obtained in Step A, to provide the crystalline potassium salt of Compound A.

All of the steps of the P3 process are optionally but preferably conducted with agitation (e.g., stirring).

This process is similar to the P2 process, except that an aqueous solution of KOH (v. potassium alkoxide in an organic solvent) is employed. The solvents disclosed above as being suitable for use as the first solvent in the P2 process are typically also suitable for use as the organic solvent in the P3 process. As used herein, the term "water-dissolving organic solvent" means that water is sufficiently soluble in the organic solvent to bring KOH in the second solution into contact with Compound A in the first solution, thereby permitting formation of a K salt of Compound A. Preferably the organic solvent and the water are employed in proportions that result in the formation of a single liquid phase in the crystallization mixture resulting from Step A3.

Compound A can be employed in the first solution at any concentration which will ultimately result in the formation of at least some of the desired crystalline potassium salt, but is typically employed in the first solution at a concentration at or close to that which provides a saturated first solution. The use of a nearly saturated to saturated first solution, in combination with a suitable final solvent volume ratio (see below), will subsequently afford a highly super-saturated K salt solution, so that the output of crystallized K salt from the process can be maximized.

Amounts of KOH suitable for use in the P3 process are typically the same as the amounts of base set forth above as suitable for use in the P1 and P2 processes. Similarly, suitable amounts of seed crystal for use in Step A3 of Process P3 and suitable temperatures for conducting Steps A3 and B3 of Process P3 are typically the same as those described above as suitable for the analogous steps in Process P2. The discussion above directed to rates of addition of the first and second solutions to the crystallizer in the P2 process applies to the rates of addition in the P3 process as well.

The volume ratio of organic solvent to water is suitably chosen to provide a solvent system in which Compound A has a relatively high solubility and the desired K salt of Compound A has a relatively low solubility, so as to afford conditions favorable to the crystallization of the K salt. Typically Compound A is more soluble in the organic solvent than is the desired K salt. On the other hand, the K salt is more soluble in water than is Compound A. Accordingly, the solvent system typically has a predominant portion of organic solvent in order to avoid or minimize loss of the K salt in the mother liquor. The final solvent volume ratio of the organic solvent to water employed in Process P3 is suitably in a range of from about 50:50 to about 99:1, is typically in a range of from about 70:30 to about 98:2, and is more typically in a range of from about 80:20 to about 97:3 (e.g., about 95:5).

Embodiments of the P3 process include the process as originally set forth above incorporating one or more of the following aspects (i) to (viii):

(i):

(i-a) the organic solvent is a di-($C_{1-4}$ alkyl) ketone, a dialkyl ether wherein each alkyl is independently a $C_{1-4}$ alkyl, a $C_{1-4}$ linear or branched alkane substituted with two —O—$C_{1-4}$ alkyl groups (which are the same or different), a $C_4$-$C_6$ cyclic ether or diether, a tri-($C_{1-4}$)alkylamine, a N,N-di-($C_{1-4}$ alkyl)-$C_{1-4}$ alkylamide, an N—($C_{1-4}$ alkyl)pyrrolidone, a di-($C_{1-4}$ alkyl)sulfoxide, or a $C_2$-$C_4$ alkanenitrile;

(i-b) the organic solvent is acetone, THF, DMF, NMP, DMSO, or acetonitrile; or (i-c) the organic solvent is acetonitrile;

(ii) KOH is employed in Step A3 in an amount in a range of from about from about 0.5 to about 1.1 equivalents (or from about 0.9 to about 1.1 equivalents, or from about 0.90 to about 1.0 equivalent, or from about 0.90 to about 0.99 equivalent) per equivalent of Compound A;

(iii) Step A3 is conducted at a temperature in a range of from about from about 0 to about 60° C. (or from about 20 to about 50° C., or from about 30 to about 50° C., or from about 40 to about 45° C.);

(iv) Step B3 is conducted at a temperature in a range of from about 0 to about 60° C. (or from about 15 to about 50° C., or from about 20 to about 40° C., or is initially conducted at a temperature in a range of from about 30 to about 40° C. and then from about 20 to about 30° C. until termination/completion);

(v) seed crystals are employed in an amount in a range of from about 1 to about 30 wt. % (or from about 10 to about 25 wt. %, or from about 15 to about 25 wt. %);

(vi) the crystallization mixture in Step A3 has a final solvent volume ratio of organic solvent to water in a range of from about 50:50 to about 99:1 (or from about 70:30 to about 98:2, or from about 80:20 to about 97:3; or about 95:5);

(vii) the crystal slurry solvent volume ratio is about the same as the final solvent volume ratio; and (viii) during the concurrent addition of the first and second solutions in Step A3, the solutions are added to the crystallizer at rates which provide a constant ratio (i.e., a fixed ratio) of equivalents of KOH to equivalents of Compound A.

Other embodiments of the P3 process include the process as originally set forth and as set forth in each of the preceding embodiments, wherein each of the processes further comprises:

(C3) recovering the crystalline K salt of Compound A from the aged mixture. In an aspect of this embodiment, the crystalline K salt is recovered by filtration to obtain a crystalline cake, optionally washing the cake with a third amount of the water, the organic solvent, or a combination thereof, and drying.

Additional embodiments of the P3 process of the invention include the process as originally set forth and as set forth in each of the preceding embodiments, wherein crystal seed employed in the process comprises Form 1 crystalline potassium salt of Compound A and the crystalline salt resulting from the process comprises Form 1 crystalline potassium salt of Compound A.

The seeding step set forth above in Process P3 is optional in the sense that crystalline Compound A K salt can be obtained without seeding. Seeding is preferred, however, as a means of inducing or assisting crystallization generally and of preparing specific crystalline forms (e.g., Form 1) particularly.

The present invention also includes a process for preparing anhydrous Form 1 crystalline potassium salt of Compound A (alternatively referred to herein as "Process P4" or the "P4 process"), which comprises:

(A4) forming a slurry of Form 2 hydrated crystalline potassium salt of Compound A in a solvent selected from the group consisting of an alkyl alcohol, a dialkyl ketone, and an alkanenitrile; and (B4) ageing the slurry, to provide the anhydrous Form 1 crystalline potassium salt of Compound A.

A class of substances suitable for use as the slurry solvent in Step A4 consists of any substance selected from the group consisting of a $C_{1-4}$ alkyl alcohol, a di-($C_{1-4}$ alkyl) ketone, and a $C_{2-4}$ alkanenitrile. A sub-class of substances that are particularly suitable as slurry solvents consists of any substance selected from a $C_{1-4}$ alkyl alcohol, acetone, and acetonitrile. A preferred slurry solvent is selected from methanol, ethanol, acetone and acetonitrile. The slurry formation in Step A4 can suitably be conducted at a temperature in a range of from about 0 to 40° C., is typically conducted in a range of from about 10 to about 40° C., and is more typically conducted in a range of from about 20 to about 40° C. (e.g., from about 20 to about 30° C.). Ageing in Step B4 is suitably conducted at the same temperature as Step A4. The ageing time can vary considerably depending upon such factors as the choice of solvent, ageing temperature, and the like, but the ageing is typically conducted for a time in a range of from about 0.5 to about 15 days.

At the conclusion of the ageing step, the resulting crystalline K salt can be recovered by conventional means, such as by filtration, an optional solvent wash (e.g., a fresh portion of slurry solvent), and drying.

The present invention also includes a process for preparing Form 2 crystalline potassium salt of Compound A (alternatively referred to herein as "Process P5" or the "P5 process"), which comprises sonicating a solution comprising Compound A, KOH, acetone, and at least a trace amount of water to obtain the Form 2 crystalline potassium salt of Compound A.

KOH is suitably employed in the P5 process in an amount in a range of from about 0.95 to about 1.1 equivalents per equivalent of Compound A, and is typically employed in an amount of about 1 equivalent per equivalent of Compound A. The sonication can be done by immersing the reaction vessel in an ultrasonic bath or otherwise equipping the vessel with an ultrasonic radiation source and conducting the sonication for a time sufficient to effect crystallization. The sonication and subsequent crystallization are suitably conducted at a temperature in a range of from about 10 to about 40° C., and typically conducted at a temperature in a range of from about 20 to about 30° C. The sonication step is suitably conducted for a time in a range of from about 0.5 to 10 minutes, and is typically conducted for a time in a range of from about 0.5 to about 2 minutes. At least a trace amount of water must be present to effect formation of the hydrated K salt of Compound A. A suitable amount of water is at least about 1 wt. % based on the weight of acetone employed in the solution. In one embodiment, water is present in an amount of from about 1 to about 3 wt. % (e.g., from about 1.2 to about 2 wt. %).

At the conclusion of the sonication step, the resulting crystalline K salt can be recovered (alternatively referred to as "isolated") by conventional means. For example, the crystalline product can be separated from the solution by filtration, optionally washed with an organic solvent (e.g., acetone), and dried (e.g., by vacuum and/or heat).

As used herein, the term "seeding" and variants thereof (e.g., "seeded") mean contacting a solution of a potassium salt of Compound A with a crystalline potassium salt of Compound A (e.g., crystalline Form 1), either per se or as a slurry in a suitable solvent, in order to induce and/or assist in crystallization of the salt from the solution.

The term "ageing" and variants thereof (e.g., "aged") mean allowing the reactants (e.g., potassium base and Compound A) to stay in contact for a time and under conditions effective for completion of the reaction (e.g., K salt formation).

A reference herein to "equivalent" or "equivalents" means molar equivalent(s).

The term "substantial" (or "substantially") as used herein means at least about 60%, preferably at least about 80%, and more preferably at least about 90% (e.g., at least about 95%). Thus, for example, a substantial portion of a time period means for at least about 60% of the time, preferably at least about 80%, etc. As another example, when a substantial portion of a binary solvent system is solvent A, then at least about 60%, preferably at least about 80%, etc. of the solvent in the solvent system is solvent A. As still another example, a substantially complete reaction is at least about 60% complete (i.e., at least 60% conversion of the reactants to desired product and/or by-product has occurred), preferably at least about 80% complete, etc.

Certain of the compounds disclosed and depicted herein have tautomeric forms. For example, the compound of Formula S (see below) has tautomeric forms including the following:

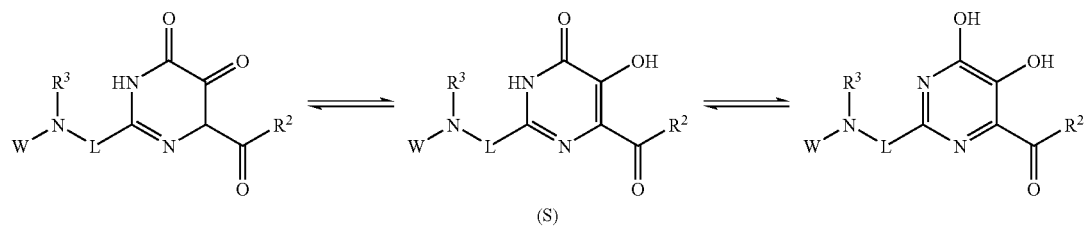

(S)

To the extent such compounds form part of the present invention, it is understood that the invention includes all tautomeric forms thereof, individually and in mixtures.

As noted above, the present invention includes administration of an effective amount of a potassium salt of Compound A (either alone or as the active component of a pharmaceutical composition) for inhibiting HIV integrase, for the treatment or prophylaxis of HIV infection, or for the treatment, prophylaxis, or delay in the onset of AIDS to a subject in need of such inhibition, treatment, prophylaxis, or delay. The present invention also includes the use of a potassium salt of Compound A in combination with an anti-HIV agent.

The term "administration" and variants thereof (e.g., "administering" a compound) in reference to a Compound A K salt of the invention mean providing the salt to the individual in need of inhibition, treatment or prophylaxis. When a potassium salt of Compound A is provided in combination with one or more other active agents (e.g., antiviral agents useful for treating or prophylaxis of HIV infection or AIDS), "administration" and its variants are each understood to include provision of the compound or prodrug and other agents at the same time (separately or together) or at different times.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. The effective amount can be a "therapeutically effective amount" for the alleviation of the symptoms of the disease or condition being treated. The effective amount can also be a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). In the present invention, the active ingredient (i.e., Compound A) is administered as a potassium salt, and references to the amount of active ingredient are to the free phenol form of Compound A.

The term "anti-HIV agent" means an agent which is effective in one or more of the following uses: inhibiting integrase or another enzyme required for HIV replication or infection, prophylaxis of HIV infection, treating HIV infection, delaying the onset of AIDS, prophylaxis of AIDS, or treating AIDS. Suitable anti-HIV agents include HIV/AIDS antiviral agents, anti-infective agents, and immunomodulators. Suitable anti-HIV agents include those listed in Table 1 as follows:

Antivirals

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nucleoside reverse transcriptase inhibitor) |
| abacavir + lamivudine + zidovudine | GlaxoSmithKline (TRIZVIR ®) | HIV infection, AIDS, ARC (nucleoside reverse transcriptase inhibitors) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (protease inhibitor) |
| ansamycin LM 427 | Adria Laboratories (Dublin, OH) Erbamont (Stamford, CT) | ARC |
| antibody which neutralizes pH labile alpha aberrant interferon | Advanced Biotherapy Concepts (Rockville, MD) | AIDS, ARC |

-continued

| Drug Name | Manufacturer (Tradename and/or Location) | Indication (Activity) |
|---|---|---|
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| capravirine (AG-1549, S-1153) | Pfizer | HIV infection, AIDS, ARC (non-nucleoside reverse transcriptase inhibitor) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (non-nucleoside reverse transcriptase inhibitor) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nuclesodie reverse transcriptase inhibitor) |
| ddI (didanosine, dideoxyinosine) | Bristol-Myers Squibb (VIDEX ®) | HIV infection, AIDS, ARC; combination with AZT/d4T (nucleoside reverse transcriptase inhibitor) |
| DPC 681 & DPC 684 | DuPont | HIV infection, AIDS, ARC (protease inhibitors) |
| DPC 961 & DPC 083 | Bristol-Myers Squibb (from DuPont Pharma) | HIV infection AIDS, ARC (non-nucleoside reverse transcriptase inhibitors) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |
| emtricitabine FTC | Gilead (EMTRIVA ®) Emory University | HIV infection, AIDS, ARC (nucleoside reverse transcriptase inhibitor) |
| emivirine | Gilead (from Triangle Pharmaceuticals) (COACTINON ®) | HIV infection, AIDS, ARC (non-nucleoside reverse transcriptase inhibitor) |
| enfuvirtide T-20 | Trimeris & Roche (FUZEON ®) | HIV infection, AIDS, ARC (fusion inhibitor) |
| HBY097 | Hoechst Marion Roussel | HIV infection, AIDS, ARC (non-nucleoside reverse transcriptase inhibitor) |
| fosamprenavir | Glaxo Smith Kline | HIV infection, AIDS, ARC (prodrug of amprenavir) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir (sulfate salt) | Merck (CRIXIVAN ®) | HIV infection, AIDS, ARC, asymptomatic HIV positive, (protease inhibitor) |
| ISIS 2922 | ISIS Pharmaceuticals | CMV retinitis |
| JE2147/AG1776 | Agouron | HIV infection, AIDS, ARC (protease inhibitor) |
| KNI-272 | Nat'l Cancer Institute | HIV-assoc. diseases |
| lamivudine, 3TC | GlaxoSmithKline (EPIVIR ®) | HIV infection, AIDS, ARC (nucleoside reverse transcriptase inhibitor) |
| lamivudine + zidovudine | Glaxo SmithKline (COMBIVIR ®) | HIV infection, AIDS, ARC (nucleoside reverse transcriptase inhibitor) |

-continued

| Drug Name | Manufacturer (Tradename and/or Location) | Indication (Activity) |
|---|---|---|
| lobucavir | Bristol-Myers Squibb | CMV infection |
| lopinavir (ABT-378) | Abbott | HIV infection, AIDS, ARC (protease inhibitor) |
| lopinavir + ritonavir (ABT-378/r) | Abbott (KALETRA ®) | HIV infection, AIDS, ARC (protease inhibitor) |
| mozenavir (DMP-450) | AVID (Camden, NJ) | HIV infection, AIDS, ARC (protease inhibitor) |
| nelfinavir | Agouron (VIRACEPT ®) | HIV infection, AIDS, ARC (protease inhibitor) |
| nevirapine | Boeheringer Ingleheim (VIRAMUNE ®) | HIV infection, AIDS, ARC (non-nucleoside reverse transcriptase inhibitor) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (NORVIR ®) | HIV infection, AIDS, ARC (protease inhibitor) |
| saquinavir | Hoffmann-LaRoche (FORTOVASE ®) | HIV infection, AIDS, ARC (protease inhibitor) |
| stavudine; d4T didehydrodeoxy-thymidine | Bristol-Myers Squibb (ZERIT ®) | HIV infection, AIDS, ARC (nucleoside reverse transcriptase inhibitor) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (protease inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| valaciclovir | GlaxoSmithKline | genital HSV & CMV infections |
| virazole ribavirin | Viratek/ICN (Costa Mesa, CA) | asymptomatic HIV positive, LAS, ARC |
| zidovudine; AZT | GlaxoSmithKline (RETROVIR ®) | HIV infection, AIDS, ARC, Kaposi's sarcoma in combination with other therapies (nucleoside reverse transcriptase inhibitor) |

Immuno-Modulators

| Drug Name | Manufacturer | Indication |
|---|---|---|
| AS-101 | Wyeth-Ayerst | AIDS |
| Bropirimine | Pharmacia Upjohn | advanced AIDS |

-continued

| Drug Name | Manufacturer | Indication |
|---|---|---|
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin ntravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids |  | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (ENBREL ®) | rheumatoid arthritis |
| infliximab | Centocor (REMICADE ®) | rheumatoid arthritis and Crohn's disease |

Anti-Infectives

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |

-continued

| Drug Name | Manufacturer | Indication |
|---|---|---|
| Pentamidine Isethionate (IM & IV) | LyphoMed (Rosemont, IL) | PCP treatment |
| Trimethoprim |  | antibacterial |
| Trimethoprim/sulfa |  | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |

-continued

| Drug Name | Manufacturer | Indication |
|---|---|---|
| Intraconazole-R51211 | Janssen Pharm. | histoplasmosis; cryptococcal meningitis |
| Trimetrexate | Warner-Lambert | PCP |

Other

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

For the purpose of inhibiting HIV integrase, treating or prophylaxis of HIV infection or treating, prophylaxis of or delaying the onset of AIDS, a potassium salt of Compound A of the present invention can be administered by any means that produces contact of the active agent with the agent's site of action. The potassium salt can be administered by any conventional means available for use in conjunction with pharmaceuticals, either as individual therapeutic agents or in a combination of therapeutic agents. It can be administered alone, but is typically administered with a pharmaceutical carrier selected on the basis of the chosen route of administration and standard pharmaceutical practice. A Compound A K salt of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the K salt and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

In a preferred embodiment, the potassium salt of Compound A is administered orally in a pharmaceutical composition comprising the Compound A K salt and hydroxypropylmethylcellulose (e.g., HPMC 2910), wherein the composition is compressed into a tablet. In another preferred embodiment, the potassium salt of Compound A is administered orally in a pharmaceutical composition comprising the Compound A K salt, a poloxamer (e.g., poloxamer 407), hydroxypropylmethylcellulose (e.g., HPMC K4M), and lactose (e.g., lactose hydrous spray dried), wherein the composition is compressed into a tablet.

A potassium salt of Compound A can be administered orally in a dosage range (all doses disclosed herein are on an active ingredient basis) of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 1000 milligrams of the active ingredient, particularly 1, 5, 10, 15, 20, 25, 50, 75, 100, 150, 200, 250, 300, 400, 500, 600, 700, 800, 900 and 1000 milligrams of the active ingredient for the symptomatic adjustment of the dosage to the patient to be treated. A preferred dosage of the potassium salt of Compound A (e.g., Form 1) for adult humans is oral administration in the form of capsules or tablets in an amount of from 100 mg to 600 mg twice per day. The specific dose level and frequency of dosage for any particular patient can vary and will depend upon a variety of factors including the patient's age, body weight, general health, sex, and diet; the mode and time of administration; rate of excretion; drug combination; and the severity of the particular condition.

The present invention also includes a process (alternatively referred to herein as "Process P6" or the "P6 process") for preparing a compound of Formula Q:

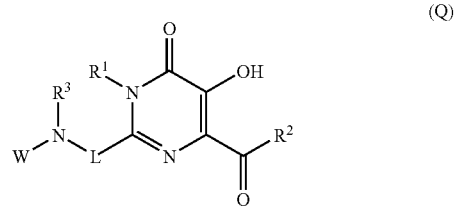

(Q)

which comprises reacting an alkyl halide of formula R$^1$X with a compound of Formula S:

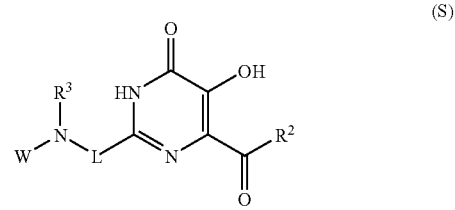

(S)

in a polar aprotic solvent and in the presence of a base selected from a magnesium base and a calcium base; wherein:

R$^1$ is C$_{1-6}$ alkyl;
R$^2$ is O—C$_{1-6}$ alkyl or N(R$^A$)R$^B$, wherein R$^A$ and R$^B$ are each independently H or C$_{1-6}$ alkyl;
R$^3$ is H or C$_{1-6}$ alkyl;
L is C$_{1-6}$ alkylene;
W is an amine-protective group; and
X is halogen.

Compounds embraced by Formula Q can be used as intermediates in the preparation of pharmacologically active substances, including Compound A and other 1-alkyl-2-aminoalkyl-5-hydroxy-6-oxo-1,6-dihydropyrimidine-4-carboxamide compounds described in WO 03/035077, wherein the compounds are HIV integrase inhibitors. The preparative route described in WO 03/035077 for these compounds involves protection of the 5-hydroxy group prior to N1-alkylation of the pyrimidine. The preparation of Compound A disclosed in WO 03/035077 and depicted in Scheme 1 below is representative:

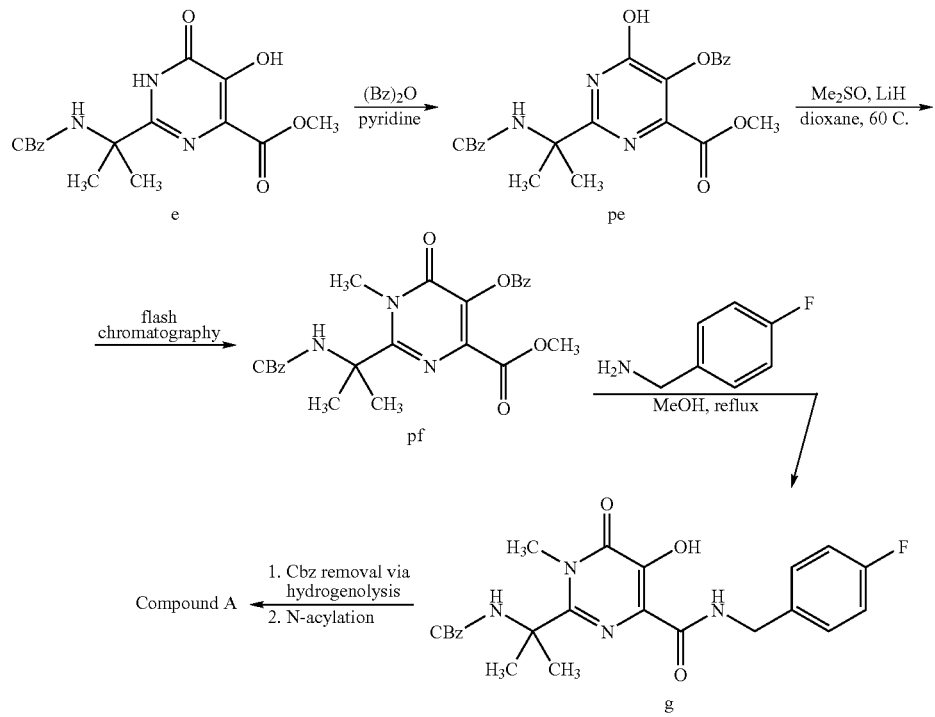

The process of the present invention constitutes an improvement over the analogous alkylation process set forth in WO 03/035077, because the present process does not require a protection step for the 5-hydroxy group. The inclusion of a protection step is a disadvantage, because the extra step can increase the complexity and cost of the process (particularly for large scale operations) and can also reduce the yield of the intermediate alkylate and the overall yield of the desired compound, in comparison to a similar process that has no protection step. Step 5 of Example 1 below illustrates the alkylation process of the present invention. The process of Step 5 of Example 1 will typically afford N1-alkylated intermediate (Compound f) in a yield equal to or better than the yield of N1-alkylated intermediate (Compound pf) obtained in the WO 03/035077 process depicted in Scheme 1.

Furthermore, the use of solvent-base combinations other than LiH-dioxane in Scheme 1 have been found not to be suitable. More particularly, other combinations (e.g., combinations of one of NaH, Cs$_2$CO$_3$, LiO-t-Bu, tetramethylguanidine, Li$_2$CO$_3$, and Na$_3$PO$_4$ with one of DME, diglyme, triglyme, DMF, THF, toluene, 1,3 dioxolane, DMAC, isopropyl acetate, EtOH, and MeCN) have been found to lead to deprotection of the benzoyl protecting group and/or selectivity favoring O-methylation; i.e, selectivity favoring:

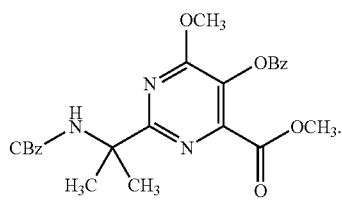

LiH in the Scheme 1 process presents a safety concern, because its use can result in the release of combustible hydrogen gas. Dioxane is carcinogenic and subject to strict emissions constraints. Accordingly, the use of the combination of LiH and dioxane, especially on a large scale, would be complex, costly, and highly unattractive. In contrast, the process of the invention employs bases other than LiH and does not require the use of dioxane. The process of the invention instead employs bases and can employ solvents, representative examples of which have been found to favor N-methylation over O-methylation of the 5-hydroxy group. This observed selectivity for N-methylation over O-methylation of the 5-hydroxy group makes protection of the 5-hydroxy group unnecessary in the process of the invention.

The base employed in Process P6 can be a magnesium-containing base or a calcium-containing base. Magnesium and calcium bases suitable for use in the process include those of formula $M(R^X)_2$, wherein M is Mg or Ca, and each $R^X$ is independently H or —O—$C_{1-6}$ alkyl. Exemplary bases include $MgH_2$, $Mg(OMe)_2$, $Mg(OH)_2$, $Mg(OEt)_2$, MgHOMe, MgHOEt, $CaH_2$, $Ca(OMe)_2$ and $Ca(OEt)_2$. The base is preferably a magnesium base. In one embodiment, the P6 process is as originally set forth above, wherein the base comprises a magnesium base of formula $Mg(R^X)_2$ where $R^X$ is as defined above. In an aspect of this embodiment, the base is a $Mg(O-C_{1-4}\text{-alkyl})_2$. In another aspect of this embodiment, the base is $Mg(OMe)_2$.

The base can be employed in any proportion with respect to Compound S and alkyl halide which results in the formation of at least some of the desired N-akylated compound of Formula Q, but the base is typically employed in a proportion which, under the reaction conditions (e.g., temperature) employed, can optimize conversion of Compound S to Compound Q. The base is suitably employed in an amount in a range of from about 0.5 to about 10 equivalents per equivalent of Compound S, is typically employed in an amount in a range of from about 1 to about 10 equivalents per equivalent of Compound S, and is more typically employed in an amount in a range of from about 1 to about 5 equivalents (e.g., from about 1.5 to about 2 equivalents) per equivalent of Compound S.

The alkyl halide employed in Process P6 is suitably of formula $R^1X$, wherein $R^1$ is $C_{1-6}$ alkyl and X is halogen (i.e., F, Cl, Br, or I). In one embodiment, the P6 process is as originally set forth above or as set forth in a preceding embodiment, wherein the alkyl halide is of formula $R^1X$, wherein $R^1$ is $C_{1-4}$ alkyl and X is chloride, bromide, or iodide. In an aspect of this embodiment, X is iodide. In another aspect of this embodiment, the alkyl halide is MeI or EtI, and in a feature of this aspect the alkyl halide is MeI.

The alkyl halide can be employed in any proportion with respect to the base and Compound S which results in the formation of at least some of the desired N-akylated compound of Formula Q, but the halide is typically employed in a proportion which, under the reaction conditions (e.g., temperature) employed will optimize conversion of Compound S to Compound Q. The alkyl halide is suitably employed in an amount in a range of from about 0.5 to about 20 equivalents per equivalent of Compound S, and is typically employed in an amount in a range of from about 1 to about 20 equivalents per equivalent of Compound S. The alkyl halide is more typically employed in an amount in a range of from about 1 to about 10 equivalents (e.g., from about 1 to 5 equivalents) per equivalent of Compound S. The alkyl halide is preferably employed in excess with respect to Compound S, such as in an amount in a range of from about 2 to about 6 equivalents (e.g., from about 3 to about 5 equivalents, or about 4 equivalents) per equivalent of Compound S.

The solvent employed in Process P6 can be any polar aprotic solvent which under the conditions employed is in the liquid phase, is chemically inert, and will dissolve, suspend, and/or disperse the reactants so as to bring them into contact and permit the formation of the desired Compound Q. The solvent is preferably one which under the conditions employed in the process favors N-alkylation to the desired Compound Q over O-alkylation to an O-alkylated by-product. The polar aprotic solvent is suitably a halogenated alkane, an ether, an ester, a tertiary amide, an N-alkylpyrrolidone, a sulfoxide, or a nitrile; and is typically a tertiary amide, an N-alkylpyrrolidone, or a sulfoxide. In one embodiment, the P6 process is as originally set forth above or as set forth in a preceding embodiment, wherein the polar aprotic solvent comprises a N,N-di-($C_{1-6}$ alkyl)-$C_{1-6}$ alkylamide, a N—($C_{1-6}$ alkyl)pyrrolidone, or a di-($C_{1-6}$ alkyl)sulfoxide. In an aspect of this embodiment, the polar aprotic solvent comprises a N,N-di-($C_{1-3}$ alkyl)-$C_{1-3}$ alkylamide, a N—(C1-3 alkyl)pyrrolidone, or a di-($C_{1-3}$ alkyl)sulfoxide. In another aspect of this embodiment, the polar aprotic solvent is DMF, DMAC, N-methylpyrrolidone, N-ethylpyrrolidone, or DMSO. In a feature of this aspect, the polar aprotic solvent is DMSO.

Process P6 can be conducted at any temperature at which the reaction (N-alkylation) forming Compound Q can be detected. The reaction can suitably be conducted at a temperature in a range of from about −20 to about 100° C., is typically conducted at a temperature in a range of from about 0 to about 100° C., and is more typically conducted at a temperature in a range of from about 15 to about 80° C. In one embodiment of the P6 process the temperature is in a range of from about 20 to about 60° C., wherein the process step is initially conducted at about 20° C. and subsequently heated to a temperature of about 60° C.

Amine protective groups suitable for use as W in Process P6 (as well as agents and conditions for their removal) are well known in the art and include, for example, those described in Greene and Wuts, *Protective Groups in Organic Synthesis,* 3d edition, (Wiley-Interscience, 1999), pp. 494-653 (herein incorporated by reference); and in McOmie, *Protective Groups in Organic Synthesis* (Plenum, 1973), pp. 44-74 (herein incorporated by reference). In one embodiment, the P6 process is as originally set forth above or as set forth in a preceding embodiment, wherein W is selected from the group consisting of:

(1) $C_{1-6}$ alkyl substituted with aryl, where the aryl is optionally substituted with from 1 to 5 substituents each of which is independently halo, —$NO_2$, —$C_{1-4}$ alkyl, or —O—$C_{1-4}$ alkyl, (2) C(=O)—$C_{1-4}$ alkyl, (3) C(=O)—$C_{1-4}$ haloalkyl, (4) C(=O)—$C_{1-4}$ alkylene-aryl, where the aryl is optionally substituted with from 1 to 5 substituents each of which is independently halo, —$NO_2$, —$C_{1-4}$ alkyl, or —O—$C_{1-4}$ alkyl, (5) C(=O)—O—$C_{1-4}$ alkyl, (6) C(=O)—O—$(CH_2)_{0-1}$—CH=$CH_2$, and (7) C(=O)—O—$C_{1-4}$ alkylene-aryl, where the aryl is optionally substituted with from 1 to 5 substituents each of which is independently halo, —$NO_2$, —$C_{1-4}$ alkyl, or —O—$C_{1-4}$ alkyl.

In an aspect of the preceding embodiment, W is selected from the group consisting of:

(1) —$CH_2$-phenyl, where the phenyl is optionally substituted with from 1 to 3 substituents each of which is independently halo, —$NO_2$, —$C_{1-4}$ alkyl, or —O—$C_{1-4}$ alkyl, (2) —C(=O)—$C_{1-4}$ alkyl, (3) —C(=O)—$CF_3$, (4) —C(=O)—$CCl_3$, (5) —C(=O)—$CH_2$-phenyl, where the phenyl is optionally substituted with from 1 to 3 substituents each of which is independently halo, —$NO_2$, —$C_{1-4}$ alkyl, or —O—$C_{1-4}$ alkyl, (6) —C(=O)—O—$C_{1-4}$ alkyl, (7) —C(=O)—O—$CH_2$—CH=$CH_2$, and (8) —C(=O)—O—$CH_2$-phenyl, where the phenyl is optionally substituted with from 1 to 3 substituents each of which is independently halo, —$NO_2$, —$C_{1-4}$ alkyl, or —O—$C_{1-4}$ alkyl.

In another aspect of the preceding embodiment, W is benzyl, acetyl, t-butyloxycarbonyl (i.e., Boc), benzyloxycarbonyl (Cbz), allyloxycarbonyl (Alloc), p-nitrobenzyloxycarbonyl, p-methoxybenzyloxycarbonyl, p-bromobenzyloxycarbonyl, p-chlorobenzyloxycarbonyl, or 2,4-dichlorobenzyloxycarbonyl. In a feature of this aspect, W is Cbz.

An embodiment of the P6 process is the process as originally set forth above, wherein $R^1$ is $C_{1-3}$ alkyl; $R^2$ is O—$C_{1-3}$ alkyl; $R^3$ is H or $C_{1-3}$ alkyl; L is $C_{1-3}$ alkylene; W is —C(=O)—O—$C_{1-4}$ alkyl, —C(=O)—O—$CH_2$—CH=$CH_2$, or —C(=O)—O—$CH_2$-phenyl, where the phenyl is optionally substituted with from 1 to 3 substituents each of which is independently halo, —$NO_2$, —$C_{1-4}$ alkyl, or —O—$C_{1-4}$ alkyl; and X is chlorine, bromine, or iodine. In an aspect of this embodiment, $R^1$ is $C_{1-3}$ alkyl; $R^2$ is O—$C_{1-3}$ alkyl; $R^3$ is H or $C_{1-3}$ alkyl; L is $CH_2$, $CH_2CH_2$, $CH(CH_3)$, or $C(CH_3)_2$; W is Boc, Alloc, or Cbz; and X is iodine.

Another embodiment of the P6 process is the process for preparing a compound of Formula Q-A:

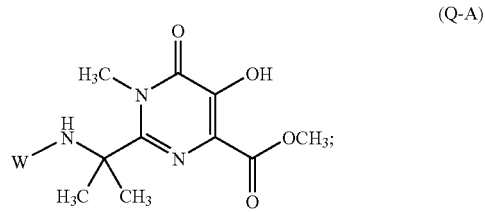

(Q-A)

which comprises reacting a methyl halide with a compound of Formula (S-A):

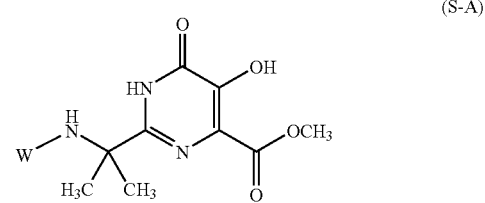

(S-A)

in a polar aprotic solvent and in the presence of a magnesium base.

Aspects of the preceding embodiment include the process as just described, incorporating one or more of the following features (i) to (vii):

(i) the magnesium base comprises $MgH_2$ or Mg(O—$C_{1-3}$ alkyl)$_2$ (or is Mg(OMe)$_2$);

(ii) the polar aprotic solvent is a N,N-di-($C_{1-3}$ alkyl)-$C_{1-3}$ alkylamide, a N—($C_{1-3}$ alkyl)pyrrolidone, or a di-($C_{1-3}$ alkyl) sulfoxide (e.g., the solvent is DMF, DMAC, N-methylpyrrolidone, N-ethylpyrrolidone, or DMSO; or the solvent is DMSO);

(iii) the reaction is conducted at a temperature in a range of from about 0 to about 100° C. (or from about 20 to about 60° C.);

(iv) the methyl halide is methyl chloride, methyl bromide, or methyl iodide (or is methyl iodide);

(v) the methyl halide is employed in an amount in a range of from about 1 to about 5 equivalents (or from about 3 to about 5 equivalents) per equivalent of Compound S-A;

(vi) the magnesium base is employed in an amount in a range of from about 1 to about 5 equivalents (or from about 1.5 to about 2 equivalents) per equivalent of Compound S-A); and (vii) W is benzyl, acetyl, Boc, Cbz, Alloc, p-nitrobenzyloxycarbonyl, p-methoxybenzyloxycarbonyl, p-bromobenzyloxycarbonyl, p-chlorobenzyloxycarbonyl, or 2,4-dichlorobenzyloxycarbonyl (or W is Cbz, so that Compound S-A is Compound e and Compound Q-A is Compound f).

Another embodiment of Process P6 is the process as originally set forth above or as described in a preceding embodiment, which further comprises recovering Compound Q from the reaction medium. Process P6 can result in the formation of O-alkylated by-product, which can be separated from the desired N-alkylated product (i.e., Compound Q) by methods known in the art such as washing the precipitated solids with suitable solvents or via chromatography. For example, Compound e can be separated from the corresponding O-alkylated by-product by washing the solids with MTBE-MeOH.

The progress of any reaction step of any chemical process set forth herein, including processes P1 to P6, can be followed by monitoring the disappearance of a reactant (e.g., Compound S) and/or the appearance of the desired product (e.g., Compound Q) using such analytical techniques as TLC, HPLC, IR, NMR or GC.

Abbreviations used herein include the following:

| | |
|---|---|
| AIDS = | acquired immunodeficiency syndrome |
| ARC = | AIDS related complex |
| AUC = | area under the curve for a plot of plasma concentration v. time to last sampling (e.g., 24 hours) |
| Bz = | benzoyl |
| Cmax = | maximum plasma concentration |
| DIEA = | diisopropylethylamine |
| DMAC = | N,N-dimethylacetamide |
| DMADC = | dimethylacetylene dicarboxylate |
| DME = | 1,2-dimethoxyethane |
| DMF = | N,N-dimethylformamide |
| DMSO = | dimethylsulfoxide |
| DSC = | differential scanning calorimetry |
| Eq. = | equivalent(s) |
| EtOAc = | ethyl acetate |
| EtOH = | ethanol |
| HIV = | human immunodeficiency virus |
| HPLC = | high-performance liquid chromatography |
| i-Pr = | isopropyl |
| IPA = | isopropyl alcohol |
| KF = | Karl Fisher titration for water |
| KOEt = | potassium ethoxide |
| LC = | liquid chromatography |
| LCAP = | LC area percent |
| LCWP = | LC weight percent |
| Me = | methyl |
| MeCN = | acetonitrile |
| MeOH = | methanol |
| MSA = | methanesulfonic acid |
| MTBE = | methyl tertiary butyl ether |
| MW = | molecular weight |
| NMM = | N-methylmorpholine |
| NMP = | N-methylpyrrolidone |
| NMR = | nuclear magnetic resonance |
| t-Bu = | tert-butyl |
| TG = | thermogravimetric |
| THF = | tetrahydrofuran |
| XRPD = | x-ray powder diffraction |

Unless expressly stated to the contrary, all ranges cited herein are inclusive. For example, a temperature range of from about 15° C. to about 80° C. means the temperature can be about 15° C., or about 80° C., or any value in between.

The following examples serve only to illustrate the invention and its practice. The examples are not to be construed as limitations on the scope or spirit of the invention.

Example 1

Preparation of Compound A and its Form 1 Crystalline Potassium Salt

Step 1: Strecker Amine Formation

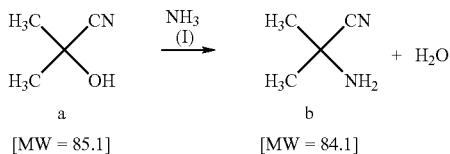

| Material | MW | Eq. | Moles | Mass | Volume | density (g/mL) |
|---|---|---|---|---|---|---|
| acetone cyanohydrin (a) | 85.1 | 1.0 | 129.3 | 11.0 kg | 11.8 L | 0.932 |
| MTBE | | 4.0 | | | 44 L | |
| ammonia (g) | 17.03 | 1.5 | 193.9 | 3.30 kg | 4.9 L | 0.674 |

Acetone cyanohydrin (11.5 kg, 12.3 L) was charged to a 5-gallon autoclave and the vessel placed under 5 psi nitrogen pressure. The autoclave was cooled to 10° C., and ammonia gas (~3.44 kg), pressurized to 30 psi, was fed into the vessel until the reaction reached complete conversion as determined by GC assay (less than 0.5% a). The resulting suspension was transferred to a polyjug and the autoclave rinsed with MTBE (approximately 17 L). The reaction mixture and rinse were then charged to a 100-L extractor followed by MTBE (15 L), the mixture agitated, and the layers carefully separated. The aqueous layer was back-extracted with MTBE (5 L) and the layers carefully separated. The organic layers were combined and charged to a 100 L flask, equipped with a batch concentrator, through an in-line filter, and the batch was concentrated (15-20° C., low vacuum) to about 20 L to remove any excess ammonia. The aminonitrile was obtained in 97% assay yield (11.1 kg) by NMR as a solution in MTBE.

Step 2: Addition of Benzyloxycarbonyl (CBz) Protective Group

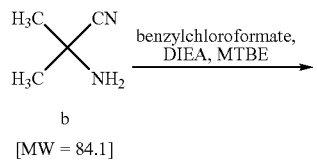

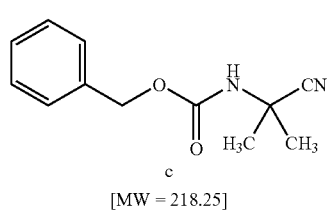

| Material | MW | Eq. | Moles | Mass | Volume |
|---|---|---|---|---|---|
| aminonitrile (b) | 84.1 | | 52.85 | 4.44 assay kg | |
| benzylchloroformate | 170.6 | 1.2 | 63.4 | 10.8 kg | |
| DIEA | 129.25 | 1.3 | 68.7 | 8.88 | |
| MTBE | | | | | 62.5 L |

To a visually clean 100-L flask containing a 5-L addition funnel, thermocouple and nitrogen inlet was charged a 59 wt. % solution of cyanoamine b in MTBE (4.44 assay kg). The solution was further diluted with MTBE (62.5 L) to bring the concentration to approximately 15 mL/g. Benzylchloroformate (1.20 equiv, 10.42 kg, 61.10 mol) was then charged in over 15 minutes via the addition funnel at such a rate as to maintain the batch temperature below 35° C. DIEA (1.3 equiv, 8.88 kg, 68.70 mol) was then added over 1.5 hours to the yellow slurry while maintaining the batch temperature below 35° C. The slurry became slightly more soluble as DIEA was added but two phases were observed when stirring was stopped. The reaction mixture was aged for 16 hours at 20-25° C., after which DI water (20 L, 4.5 mL/g) was charged into the batch. The batch was then transferred to a 100-L extractor and the phases were separated. The organic layer was then washed with 3×10 L of water and then 15 L of brine. The organic layer was transferred via a 10 μm inline filter to a 100 L round bottom flask and subsequently solvent switched to 90:10 heptane:MTBE. Crystallization occurred during the solvent switch and the resulting white crystalline product was filtered and washed with 3×5 L of 90:10 heptane:MTBE. A total of 10.1 kg of product (88% yield) was obtained in greater than 99 HPLC A %. A total of 26.7 kg of product was obtained in 3 batches with an average isolated yield of 86%.

Step 3: Amidoxime Formation

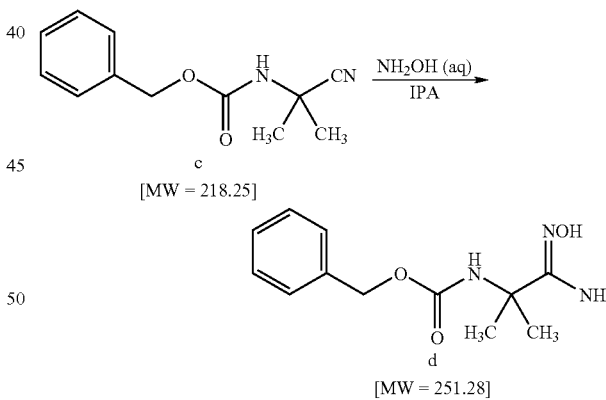

| Material | MW | Eq. | Mass | Volume |
|---|---|---|---|---|
| protected aminonitrile (c) | 218.25 | 1 | 15 g | |
| NH₂OH (50 wt. % in water) | | 1.2 | | 5.05 mL |
| IPA | | | | 40 mL + 10 mL |
| n-heptane | | | | 40 mL + 50 mL |

A solution of aminonitrile (15 g) in IPA (40 mL) was warmed to 60° C. with stirring and NH₂OH in water (5.05 μL) was added at this temperature over the course of 20 minutes.

The clear mixture was then aged at 60° C. for 3 hours, wherein product began to crystallize out of solution at this temperature after 2 hours. The slurry was then cooled to 0°-5° C. and n-heptane (40 mL) was added dropwise over 20 minutes. After stirring for 2 hours at 0°-5° C., the slurry was filtered and the cake was washed with a 20% IPA in heptane solution (60 mL), and then dried under vacuum with a nitrogen stream at room temperature to give pure amide oxime in 88% yield.

Step 4: Formation of Hydroxypyrimidinone

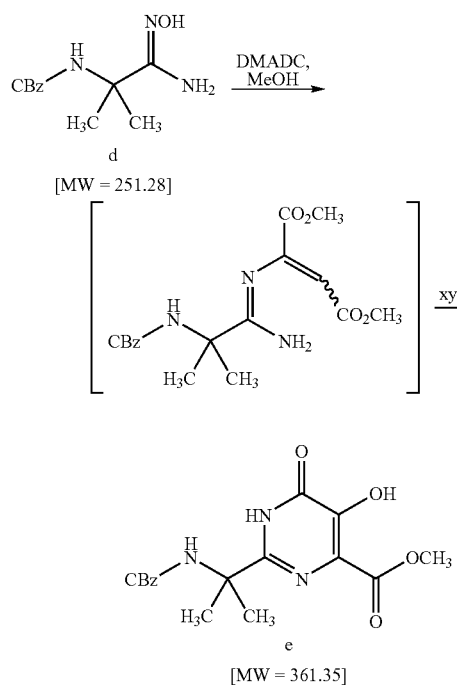

and aged 1 hour before filtration. The solids were displacement washed with 10% MeOH/MTBE (6 L then 4 L; prechilled to 0° C.) and dried on the filter pot under a nitrogen sweep to afford 2.17 kg (51.7% corrected yield; 99.5 wt %).

HPLC method: Column: Zorbax C-8 4.6 mm×250 mm; 40% ACN/60% 0.1% $H_3PO_4$ to 90% ACN/10% 0.1% $H_3PO_4$ over 12 minutes, hold 3 minutes then back to 40% ACN over 1 minute. Retention times: amidoxime d—2.4 minutes, DMAD-6.7 minutes, intermediate adducts—8.4 and 8.6 minutes (8.4 minute peak cyclizes faster), product e—5.26 minutes, xylenes—several peaks around 10.4-10.7 minutes.

Step 5: N-Methylation

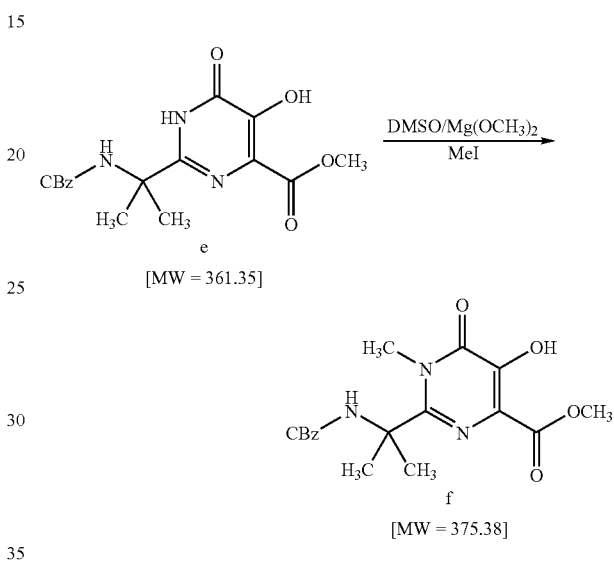

| Material | MW | Eq. | Mass | Volume | Density (g/mL) |
|---|---|---|---|---|---|
| amidoxime (d) | 251.28 | 1 | 2.9 kg | | |
| DMADC | 142.11 | 1.08 | 1.77 | | 1.16 |
| MeOH | | | | 12 L + 6 L | |
| xylenes | | | | 15 L | |
| MTBE | | | | 9 L | |

To a slurry of amidoxime (2.90 kg) in methanol (12 L) was added dimethyl acetylenedicarboxylate (1.77 kg) over 20 minutes. A slow exotherm ensued such that the temperature of the slurry increased from 20° C. to 30° C. over 15-20 minutes. After 1.5 hours, HPLC indicated greater than 95% conversion to the intermediate cis/trans adducts. The solvent was then switched to xylenes under reduced pressure (maximum temperature=50° C.), wherein 2 volumes [2×7.5 L] were added and reduced to a final volume of 7.5 L. The reaction mixture was then heated to 90° C. and kept at this temperature for 2 hours, while flushing the remaining MeOH out with a nitrogen sweep. The temperature was then increased in 10° C. increments over 3.5 hours to 125° C. and held at this temperature for 2 hours. The temperature was then finally increased to 135° C. for 5 hours. The reaction mixture was then cooled to 60° C. and MeOH (2.5 L) was added. After 30 minutes MTBE (9 L) was added slowly to build a seed bed. The batch was then cooled to 0° C. for 14 hours, and then further cooled to −5° C.

| Material | MW | Eq. | Mass | Volume |
|---|---|---|---|---|
| pyrimidine diol (e) | 361.35 | 1 | 2 kg | |
| Mg(OMe)$_2$, 8 wt. % in MeOH | | 2 | 11.95 kg | 13.4 L |
| MeI | | 4 | 3.14 kg | 1.38 L |
| DMSO | | | | 16 L |
| 2M HCl | | | | 20 L |
| MeOH | | | | 14 L |
| Na bisulfite 5 wt. % in water | | | | 2 L |
| water | | | | 60 L |

To a solution of the pyrimidine diol e (2 kg) in DMSO (16 L) was added a solution of Mg(OMe)$_2$ in MeOH (11.95 kg), after which excess MeOH was evaporated under vacuum (30 mm Hg) at 40° C. for 30 minutes. The mixture was then cooled down to 20° C., after which MeI (1.38 L) was added and the mixture stirred at 20-25° C. for 2 hours, and then at 60° C. for 5 hours under pressure in a closed flask. HPLC showed that the reaction was complete. The mixture was then cooled to 20° C., after which MeOH (14 L) was added, followed by the slow addition of 2 M HCl (20 L) [exotherm] over 60 minutes. Sodium bisulfite (5 wt. %, 2 L) was then added to quench excess I2, with the solution turning white. Water (40 L) was then added over 40 minutes and the slurry stirred for 40 minutes in an ice bath, and then filtered. The filter cake was washed first with water (20 L) and then with MTBE:MeOH 9/1 (30 L) to remove O-methylated by-product. HPLC showed less than 0.5 A % O-methylated product after washing. The solid was dried overnight at room temperature under vacuum with an N$_2$ stream to give 1.49 kg of N-methylpyrimidone (70% yield, corrected for purity of starting material and product).

Step 6: Amine Coupling

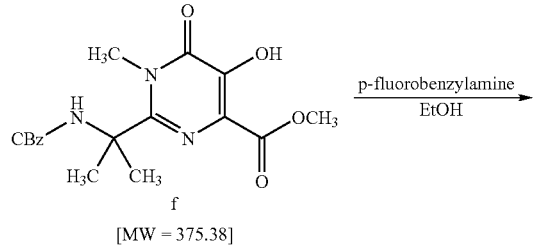

[MW = 375.38]

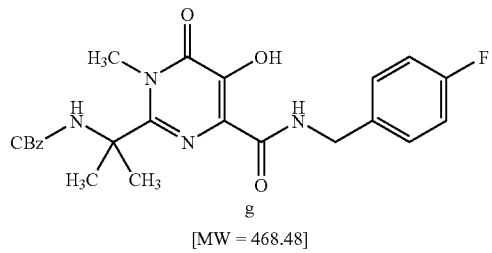

[MW = 468.48]

| Material | MW | Eq. | Mass | Volume |
|---|---|---|---|---|
| N-methylpyrimidinone (f) | 375.38 | 1 | 1.4 kg | |
| 4-fluorobenzylamine | 125.15 | 2.2 | 1.05 kg | |
| EtOH | | | | 14 L |
| water | | | | 14 L |
| acetic acid | | | | 0.55 L |

To a slurry of N-methylated pyrimidinone f (1.4 kg) in EtOH (14 L) at 4° C. was slowly added 4-fluorobenzylamine (1.05 kg) over 15 minutes, wherein an exotherm to 9° C. was observed during addition of the first 1 mole equivalent of the amine. The slurry became very thick and vigorous stirring was required. The reaction was warmed to 72° C. over 2 hours and maintained at this temperature for 1 hour and 45 minutes. The solution became extremely viscous at 45° C. where a small exotherm was observed to 50° C., after which the slurry slowly freed up and became homogeneous after 1 hour at 72° C. An HPLC sample assay (HPLC method was similar to that employed in Step 4 above) at the end of the reaction showed less than 0.5 A % N-methylated pyrimidinone. The reaction was then cooled to 60° C. and acetic acid (0.55 L) was added over 30 minutes, followed by the addition of water (6.7 L) over 30 min and then the addition of seed (3.0 g) to initiate crystallization. After 30 min at 60° C., more water (7.3 L) was added over 30 minutes and the reaction mixture allowed to cool to ambient temperature overnight. After 13 hours, the temperature was at 20° C., at which point the reaction mixture was filtered and the slurry washed with 50% water/EtOH (2×4 L). The solids were dried on the filter pot under vacuum/$N_2$ flow to a constant weight to afford a white solid product (1.59 kg; 90% corrected yield; 99% LCWP and 99.7% LCAP as determined by HPLC method similar to that employed in Step 4 above.)

Step 7: Hydrogenation of Cbz-Amide

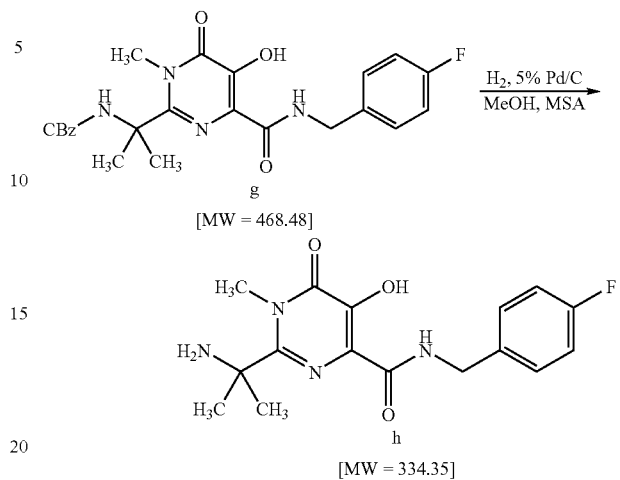

[MW = 468.48]

[MW = 334.35]

| Material | MW | mmoles | Mass | Volume |
|---|---|---|---|---|
| CBz amide (g) | 468.48 | 21.33 | 10 g | |
| MeOH | | | | 80 mL |
| 5% Pd/C (50% wet) | | | 0.15 g | |
| MSA | 96.1 | 22.4 | | 1.45 mL |
| water | | | | 8 mL |
| cake wash (4:1 MeOH:$H_2O$) | | | | 20 mL |
| 1 N NaOH | | 22.4 | | 22.4 mL |
| final cake wash (water) | | | | 30 mL |

A stainless steel hydrogenation vessel was preconditioned with MeOH, Pd/C catalyst and MSA under the reaction conditions described below. Cbz-amide g (10 g) was then slurried in MeOH (80 mL) in the preconditioned vessel. MSA (1.45 mL) was added to the slurry in one portion at room temperature. 5% Pd/C (0.15 g, 50% wet) was also added to the hydrogenation vessel. Hydrogen was charged to the vessel in three successive vacuum/hydrogen purge cycles, after which the mixture was hydrogenated at 40 psig for 3-4 hour at 50° C. Following hydrogenation, water (8 mL) was added to the reaction mixture, the mixture was stirred, and the catalyst was filtered and washed with 4:1 MeOH:water (20 mL). The pH of combined filtrates was adjusted to pH 7 to 8.0 by slow addition of 1 N NaOH (22.4 mL), which precipitated a solid. The slurry was stirred at 0-5° C. for 4 hours and the solid filtered, washed with water (30 mL), collected and dried in vacuo at 50° C. The product amine (as hydrate) was obtained as a white crystalline solid (7.7 g) in 96% yield (corrected for KF), 89% LCWP, 99.8% LCAP, KF=11 wt. %

HPLC Method A (product assay): column: 25 cm×4.6 mm Zorbax RX-C8; mobile phase: A=0.1% $H_3PO_4$, B=$CH_3CN$, 0 minutes (80% A/20% B), 20 minutes (20% A/80% B), 25 minutes (20% A/80% B); flow: 1.0 mL/minute; wavelength: 210 nm; column temperature: 40° C.; retention times: desfluoroamine byproduct—5.5 min, amine product—5.85 minutes, toluene—16.5 minutes, Cbz-amide—16.82 minutes.

HPLC Method B (product purity): column: 25 cm×4.6 mm YMC-basic; mobile phase: A=25 mmol $KH_2PO_4$ adjusted to pH=6.1, B=$CH_3CN$, 0 minutes (90% A/10% B), 30 minutes (30% A/70% B), 35 minutes (30% A/70% B); flow: 1 mL/minute; wavelength: 210 nm; column temperature: 30°

C.; retention times: des-fluoroamine—9.1 minutes, amine—10.1 minutes, toluene—24.2 minutes, Cbz amide—25.7 minutes.

Step 8: Oxadiazole Coupling

Part A: Preparation of Oxadiazole K Salt

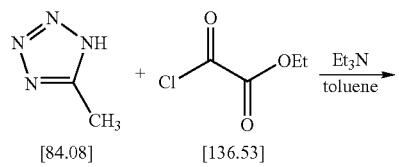

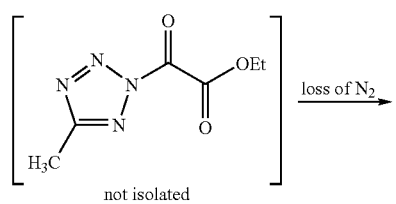

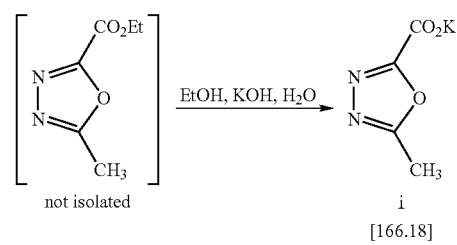

| Material | Eq. | Mole | Mass | Volume | Density |
|---|---|---|---|---|---|
| 5-methyltetrazole (96 wt. %) | 1.0 | 28.54 | 2.5 kg (2.4 kg) | | |
| ethyloxalyl chloride | 1.03 | 29.4 | 4.014 kg | 3.29 L | 1.22 |
| triethylamine | 1.05 | 29.97 | 3.033 kg | 4.21 L | 0.72 |
| toluene | | | | 74 L | |
| EtOH (punctilious) | | | | 61 L | |
| MTBE | | | | 15 L | |
| KOH aq. *20 wt. %) | | | | 8 L | |
| 10% brine | | | | 5 L | |

Ethyl oxalylchloride (4.01 kg) was slowly added to a mixture of 5-methyltetrazole (2.50 kg), triethylamine (3.03 kg) in toluene (32 L) at 0° C. at such a rate that the temperature stays below 5° C. The resulting slurry was stirred for 1 hour at 0-5° C. then the triethylamine/HCl salt was filtered off. The solid was washed with 27 L of cold toluene (5° C.). The combined filtrates were kept at 0° C. and were slowly added to a hot solution of toluene (50° C., 15 L) over 40-50 minutes ($N_2$ gas evolution), then the solution was aged at 60-65° C. for 1 hour. After cooling at 20° C., the toluene solution was washed with 5 L of 10% brine, then solvent switched to ethanol (reduced to 8 L, then 17 L of EtOH was added, then concentrated down to 8 L, then 33 liters of EtOH were added to adjust final volume of 41 L). The ethanol solution was cooled to 10° C. and KOH aq. (8.0 L) was added over 30 minutes, and the resulting thick slurry was then stirred for 40 minutes at room temperature while the oxadiazole K salt crystallized out. The solid was filtered off, washed with 11 L of EtOH and finally with 15 L of MTBE. The solid was dried overnight under vacuum at 20° C. with a nitrogen stream to yield 4.48 kg (90.8%) of the K-salt i.

Part B: Oxadiazole Coupling

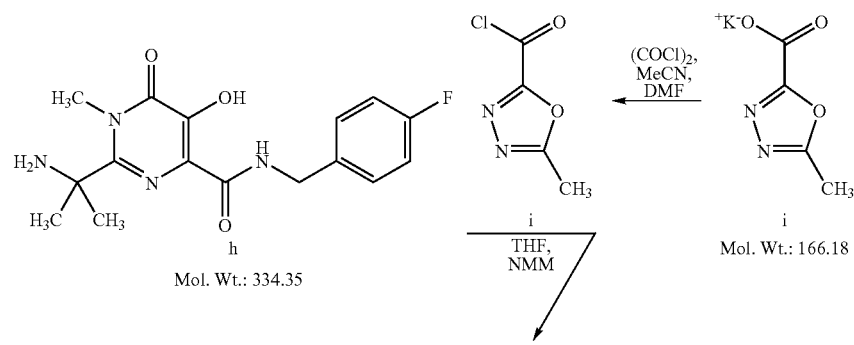

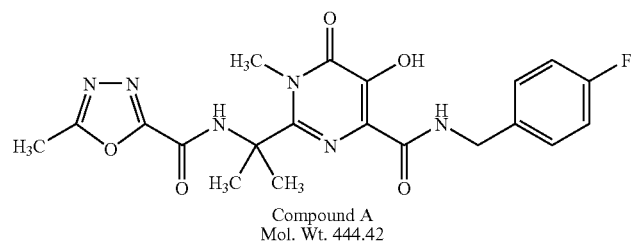

Compound A
Mol. Wt. 444.42

| Reagent | Mass | mL | Moles | Eq. |
| --- | --- | --- | --- | --- |
| oxadiazole K salt i | 33.8 g (96.1 wt %) | | 0.20 | 2.2 |
| MeCN | | 280 mL | | |
| DMF | 0.33 | | | |
| oxalyl chloride | 23.7 g | 16.3 mL | 0.19 | 2.1 |
| free amine h | 30 g (99 Wt %) | | 0.089 | 1 |
| THF | | 821 mL | | |
| NMM | 21.56 g | 23.4 mL | 0.21 | 2.4 |
| $NH_4OH$ (30% in $H_2O$) | 62.3 g | 69 mL | 0.53 | 6 |
| HCl (2N) | | 500 mL | | |
| IPA | | 920 mL | | |
| water | | 400 mL | | |
| MeOH | | 300 mL | | |

A 500 mL round bottom flask was charged with oxadiazole K salt i (33.8 g) followed by MeCN (280 mL) and DMF (0.33 mL) with strong stirring. The resulting slurry was then cooled down to 0-5° C. and oxalyl chloride (23.7 g) was added over the course of 20 minutes in order to maintain the internal temperature at less than 5° C. The resulting acyl chloride-containing slurry was then aged for 1 hour.

To a 2 L round bottom flask the free amine h (30 g) was added followed by THF (821 mL). The resulting slurry was cooled down to 0-5° C., after which NMM (21.56 g) was added and the slurry so obtained was stirred for 10 minutes at the cold temperature. The previously prepared acyl chloride-containing slurry was added slowly to the free amine slurry over the course of 20 minutes such that the temperature did not exceed 5° C. The slurry was then aged for 1.5 hours at 0-5° C. At this time HPLC showed no more amine h (<0.5% LCAP, 100% conversion). The reaction mixture was then quenched with $NH_4OH$ (30% in water) (69 mL) which was added over the course of 3 minutes. The resulting yellow slurry was then stirred for an additional hour at temperatures less than 10° C. The yellow slurry was then acidified to pH 2-3 with HCl (2N) (500 mL). To the resulting red wine colored solution, IPA (920 mL) was added. The low boiling point organic solvents were then evaporated under reduced pressure (40 torr) at room temperature to a final solution volume of 1100 mL, at which volume crystalline Compound A began to precipitate. Water (400 mL) was then added to this new slurry over the course of 10 minutes, and the slurry aged overnight at room temperature. The aged slurry was filtered and the solid obtained was washed with water (170 mL), followed by a swish wash with cold MeOH (300 mL, previously cooled in an ice bath), and finally by a swish wash with water (700 mL). The solid so obtained was dried overnight under vacuum and nitrogen stream to give 35.5 g of Compound A (91% yield).

Step 9: Formation of a Crystalline Potassium Salt of Compound A

Acetonitrile (50 mL) and anhydrous Compound A (5.8 g, 97.4 wt. %) were charged at room temperature to a jacketed 125 mL round bottom flask equipped with a mechanical stirrer and equipped with a nitrogen inlet (i.e., the crystallization was conducted under nitrogen). The resulting slurry was agitated at 45° C. until the solids were completely in solution. Form 1 crystalline Compound A K salt was then charged to the solution as seed (0.184 g, 3 wt % to theoretical K salt). Aqueous KOH 30% w/v solution (0.98 eq., 2.33 mL, 0.0125 moles) was then added with the following charge profile while maintaining batch at 45° C.:

0.466 mL over 5 hours, 0.0932 mL/hr (20 mol %)
1.864 mL over 7 hours, 0.2663 mL/hr (80 mol %)

The resulting slurry was cooled to 20° C. and aged at 20° C. until the concentration of Compound A in the mother liquor was measured to be less than 4 g/L. The batch was filtered, the cake washed with MeCN (3×12 mL), and then dried under vacuum at 45° C., with a small nitrogen sweep, until the amount of MeCN and water present as determined by thermogravimetric analysis was less than 1 wt. %. The K salt of Compound A was obtained in >99 A % by HPLC analysis.

Example 2

Form 1 Crystalline Potassium Salt of Compound A

Part A: Preparation

Ethanol (147 mL), water (147 µL), and Compound A (97.9 g assay by HPLC) were charged to a 1 L round bottom flask equipped with mechanical stirrer, addition funnel, nitrogen inlet (i.e., run conducted under nitrogen), and a thermocouple. Aqueous KOH (45% w/w, 0.98 eq., 18.5 mL, 216 mmoles) was added to the suspension over 10 minutes at 21° C. The resulting suspension was agitated for 0.5 hour resulting in the dissolution of a majority of the solids, after which the batch was filtered through a 1 µm filter directly into a 5 L round bottom flask equipped with mechanical stirrer, addition funnel, nitrogen inlet, and thermocouple. The 1 L flask was rinsed with 1:1 (v/v) water/EtOH (48 mL) and the rinse was filtered into the 5 L crystallization vessel. The filtered solution was seeded with crystalline Form 1 Compound A K salt (200 mg) at room temperature and then aged for 1 hour to build a good seed bed, after which the suspension was diluted with EtOH (1.57 L) at 20° C. over 1.5 hour. The batch was then cooled to about 4° C. and aged until the concentration of Compound A in the mother liquor was measured to be 4.7 g/L. The batch was filtered, the crystallization vessel rinsed with 50 mL EtOH into the filter, the cake washed with EtOH (4×100 mL), and then dried under vacuum and a nitrogen tent until the amount of EtOH present by NMR was about 0.4 mol % relative to the potassium salt. The potassium salt of Compound A was obtained in 88% yield (91.5 g assay by HPLC, 99 area % by HPLC analysis).

Part B: Characterization

An XRPD pattern of a K salt prepared in the manner described in Part A was generated on a Philips Analytical X'Pert Pro X-ray powder diffractometer using a continuous scan from 2.5 to 40 degrees 2 Θ over about 12 minutes (i.e., 0.02° step size with 40 seconds/step), 2 RPS stage rotation, and a gonio scan axis. Copper K-Alpha 1 ($K_{\alpha 1}$) and K-Alpha 2 ($K_{\alpha 2}$) radiation was used as the source. The experiment was run under ambient conditions. The XRPD pattern is shown in FIG. 1. 2Θ values and the corresponding d-spacings include the following:

| Peak No. | d-spacing (Å) | 2 Theta |
| --- | --- | --- |
| 1 | 14.9 | 5.9 |
| 2 | 7.1 | 12.5 |
| 3 | 4.4 | 20.0 |
| 4 | 4.3 | 20.6 |
| 5 | 3.5 | 25.6 |

Figure 2:
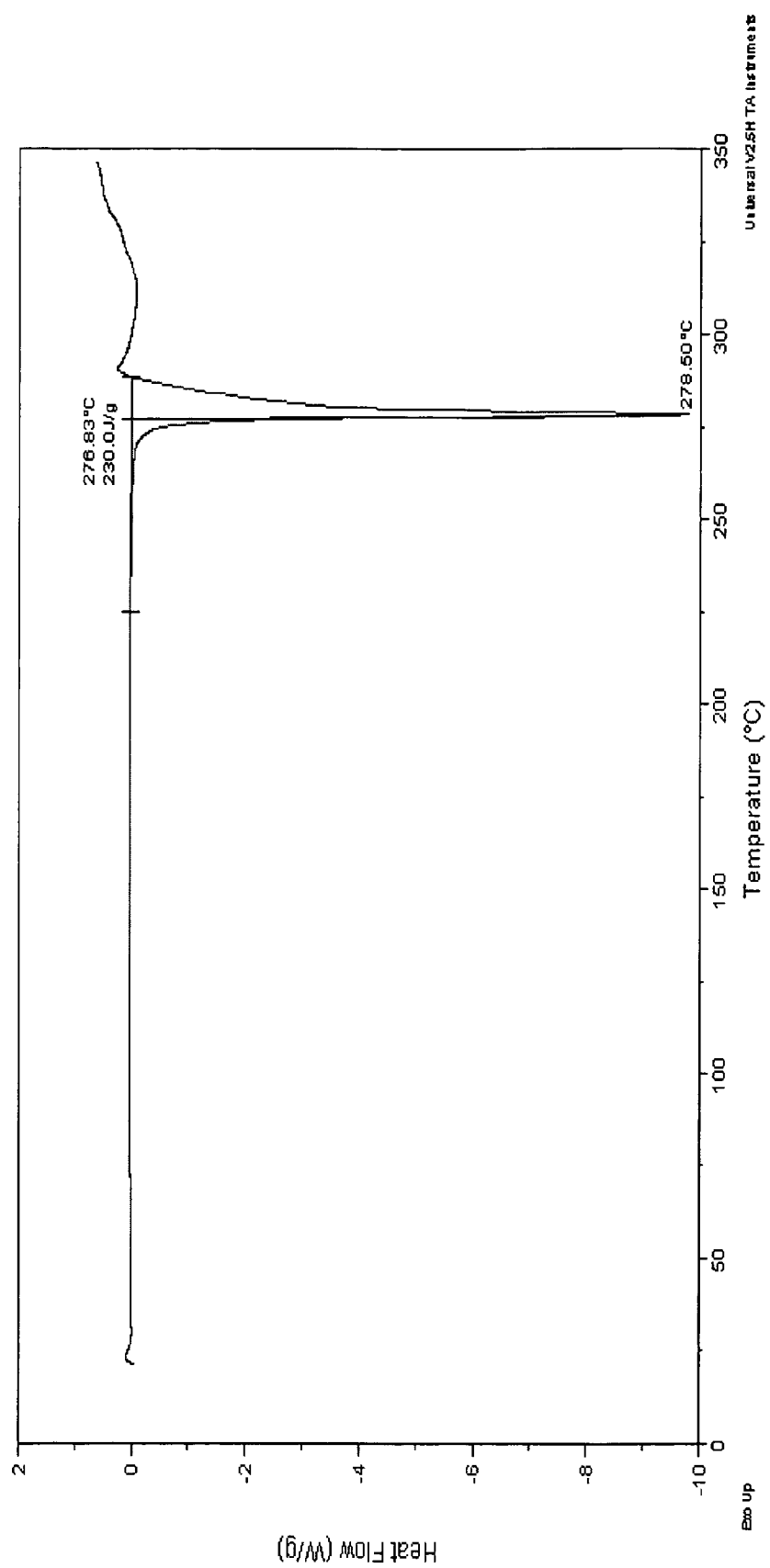
FIG. 2 is the DSC curve for the potassium salt of Compound A as prepared in Example 2.

A K salt prepared in the manner described in Part A was also analyzed by a TA Instruments DSC 2910 differential scanning calorimeter at a heating rate of 10° C./min from room temperature to 350° C. in a crimped pinhole aluminum pan in a nitrogen atmosphere. The DSC curve, shown in FIG. 2, exhibited a single, sharp endotherm with a peak temperature of about 279° C. and an associated heat of fusion of about 230.0 J/gm. The endotherm is believed to be due to melting.

A thermogravimetric analysis was performed with a Perkin-Elmer Model TGA 7 under nitrogen at a heating rate of 10° C./min from room temperature to about 350° C. The TG curve showed a 0.3% weight loss during heating to 250° C.

Hygroscopicity data was obtained on a VTI Symmetrical Vapor Sorption Analyzer Model SGA-1. Data was collected at room temperature from 5-95% relative humidity and back, 5% relative humidity change per step. Equilibrium conditions were 0.01 weight percent change in 5 minutes with a maximum equilibration time of 180 minutes. The data indicated that the material had a 1.8% weight increase when equilibrated at 95% RH at 25° C. When equilibrated back down to 5% RH, the material returned back to approximately its dry weight. An XRPD analysis of the material after the hygroscopicity experiment showed that the material had not changed phases.

K salt prepared as described in Part A was also assayed by HCl titration using a Brinkmann Metrohm 716 DMS Titrino. The assay results indicated the salt was a monopotassium salt.

Example 3

Form 1 Crystalline Potassium Salt of Compound A

Compound A (45 g) was dissolved in 50:50 v/v EtOH: MeCN (434 mL) at 35° C. to give a solution with a concentration of 96 g/L. A solution of KOEt in EtOH (38 g, 24 wt. % KOEt) was mixed with EtOH (342 g) to give a 2.4 wt. % solution of the ethoxide in ethanol. A seed bed (Form 1 crystalline K salt of Compound A) was prepared by adding the K salt (9.1 g) to 70:30 ethanol:aceontitrile (177 mL), after which the seeds were wet milled for 30 minutes using an IKA Model T50 wet mill to provide a seed bed of approximately 48,600 particle counts (i.e., a particle size range of from 1 to 500 μm) and a mean particle size of 10.4 μm.

Seed slurry (186 mL) was charged to a crystallizer, and all of EtOH:MeCN solution of Compound A was charged to a jacketed syringe pump. The syringe pump jacket was maintained at 45° C. and the crystallizer jacket was maintained at 37° C. to provide a 35° C. batch temperature. The Compound A solution and the KOEt solution were then concurrently added to the crystallizer while maintaining the batch temperature at 35° C. For the first 5 hours of the addition, the Compound A solution was added at a rate of 0.29 mL/minute, and the KOEt solution was added at a rate of 0.23 mL/minute, after which the charge rates were changed for the next 7 hours to 0.83 mL per minute for the Compound A solution and 0.66 mL/minute for the KOEt solution. At the end of the 7 hours (12 hours total addition time), all of the Compound A solution had been charged, and the KOEt addition was continued at 0.66 mL/minute until all of the solution was charged. Following the addition, the batch was cooled from 35° C. to 20° C. over 3 hours, then aged at 20° C. for 2.5 hour and filtered. After filtration, the resulting cake was washed with EtOH (3×45 mL) in a displacement/slurry/displacement wash sequence, then blown with nitrogen for 1 hour, and then dried overnight in a vacuum oven at 45° C., to afford an isolated yield of crystalline Compound A K salt of 94%.

Example 4

Form 2 Crystalline Potassium Salt of Compound A

Solid KOH (47.9 mg) and Compound A (402.4 mg) were added to acetone (8 mL), and the resulting solution was sonicated using a Fisher Scientific Ultrasonic Model FS3OH at 40 kHz for several minutes until a precipitate formed. Sample was then suction filtered to dryness.

Figure 3:
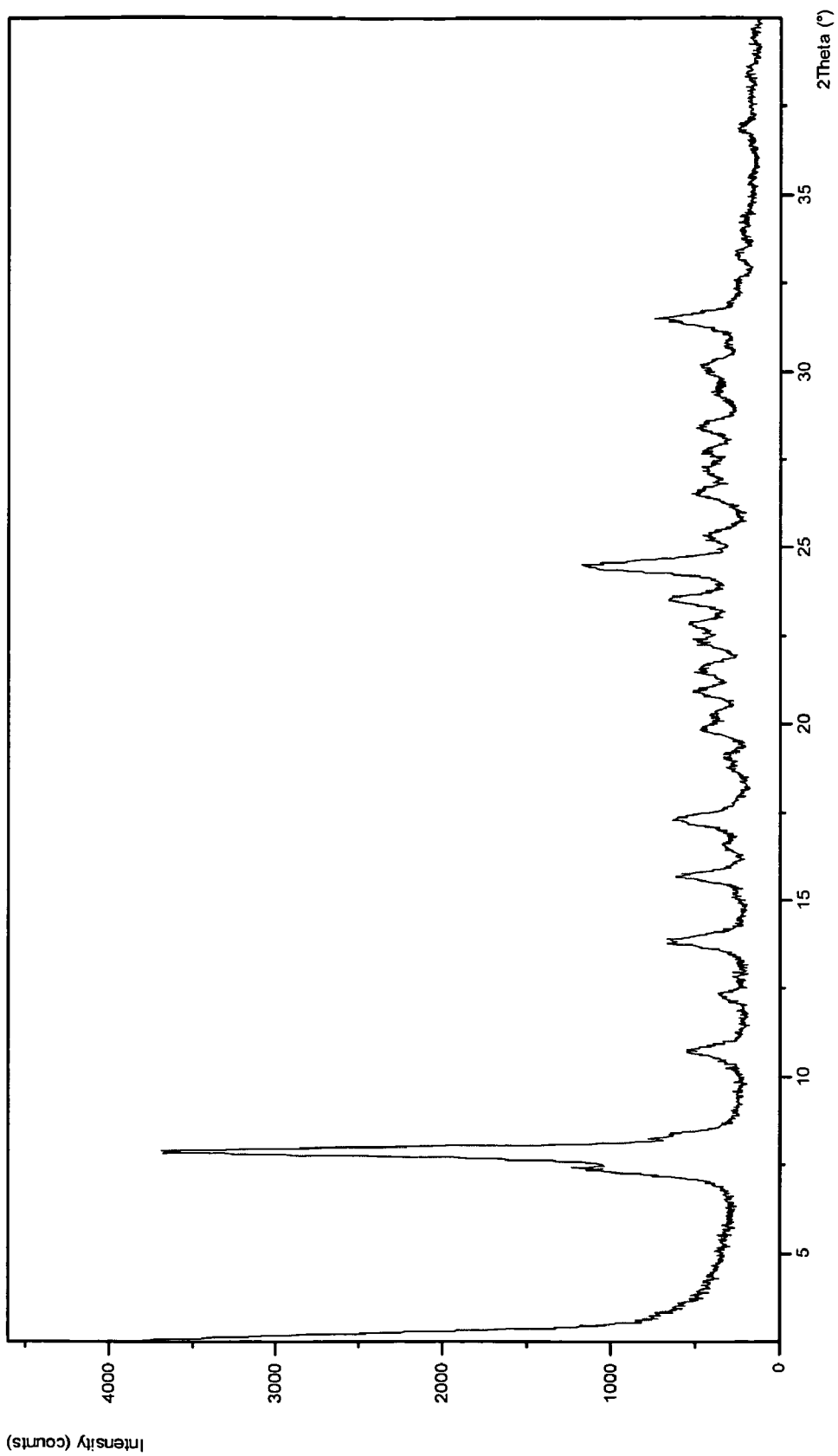
FIG. 3 is the X-ray powder diffraction pattern for the potassium salt of Compound A as prepared in Example 4.

An XRPD pattern of the isolated crystalline potassium salt prepared in the manner just described was obtained using the same instrument and settings employed in Example 2. The XRPD pattern is shown in FIG. 3. 2Θ values and the corresponding d-spacings include the following:

| Peak No. | d-spacing (Å) | 2 Theta |
|---|---|---|
| 1 | 11.2 | 7.9 |
| 2 | 6.4 | 13.8 |
| 3 | 5.7 | 15.7 |
| 4 | 3.6 | 24.5 |
| 5 | 2.8 | 31.5 |

Figure 4:
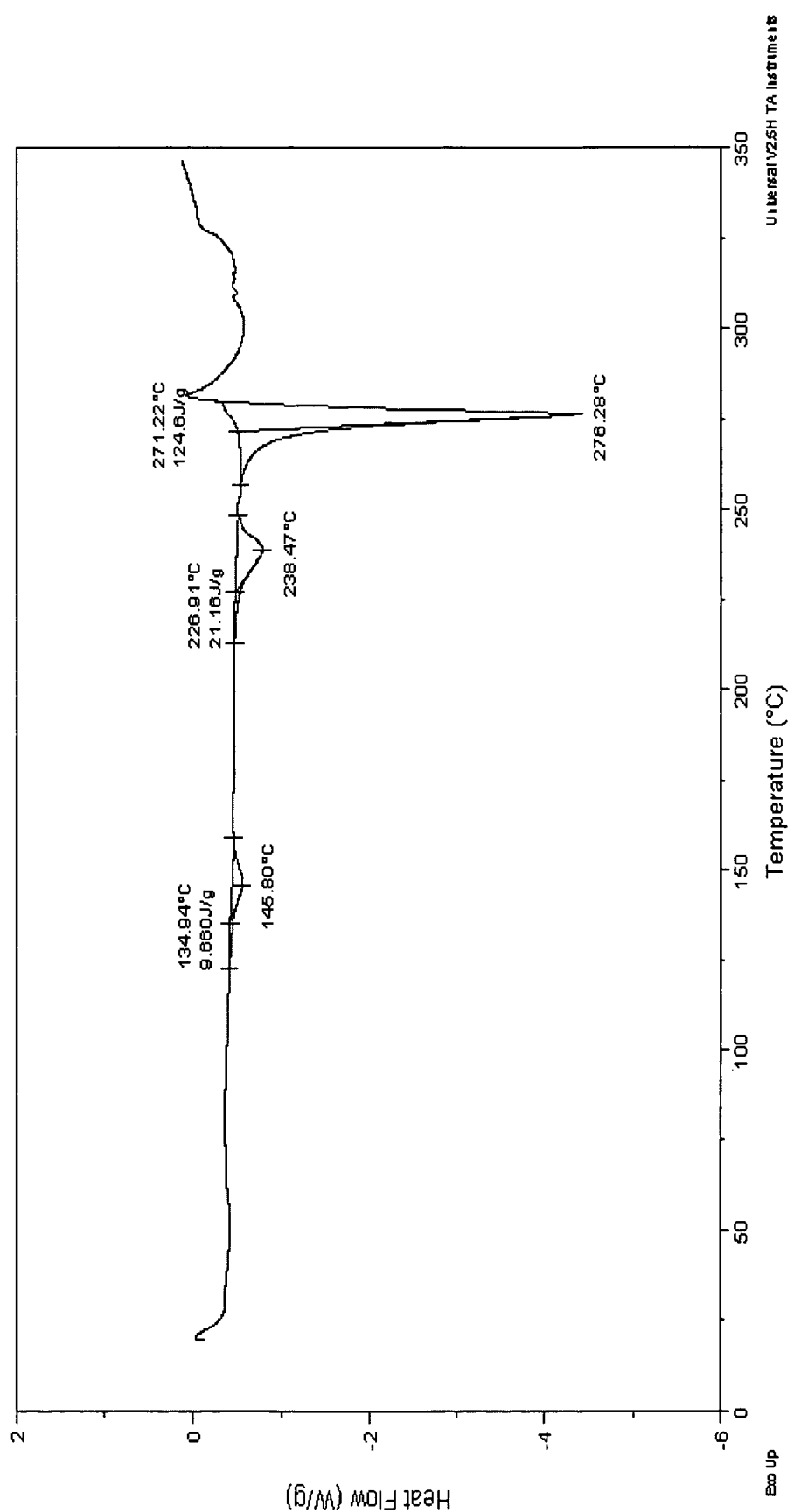
FIG. 4 is the DSC curve for the potassium salt of Compound A as prepared in Example 4.

K salt prepared in the manner just described was analyzed by a TA Instruments DSC 2920 differential scanning calorimeter at a heating rate of 10° C./min from room temperature to 350° C. in a crimped pinhole aluminum pan in a nitrogen atmosphere. The DCS curve, shown in FIG. 4, exhibited a broad endotherm at about 146° C. that is believed to be due to desolvation (associated heat of fusion=9.66 J/gm), a broad endotherm at about 238° C. believed to be due to a phase change to Form 1 (heat of fusion=21.16 J/gm), followed by a sharp endotherm at about 276° C. believed to be due to the melting of Form 1 (heat of fusion=124.6 J/gm). The difference in peak temperature and heat of fusion here as compared to the corresponding values obtained for Form 1 in Example 2 may be due, inter alia, to differences in the crystalline samples (e.g., differences in impurity level or crystal imperfections) and/or to incomplete conversion to Form 1 in this DSC scan and some subsequent decomposition during the melting of Form 1.

Thermogravimetric analyses performed in the manner described in Example 2 were done on several samples of the crystalline K salt prepared in the manner described in this Example. The results indicate that the material (crystalline Form 2) is a variable solvate that loses from about 1.6 to about 3.5% volatiles during heating up to 200° C. TG-mass spectroscopy and KF titrations done on the samples indicate that Form 2 contains water. The source of the water found in Form 2 might be water present as an impurity in the acetone and/or solid KOH used in the crystallization procedure. When Form 2 was heated beyond the desolvation temperature and allowed to age, it rehydrated readily. XRPD studies have shown that, when Form 2 is heated beyond the desolvation temperature but below the transition temperature for the conversion to Form 1, the phase was unchanged, indicating that Form 2 may be isomorphous. Samples of Form 2 heated above 240° C. and then analyzed by XRPD were found to have partially converted to Form 1.

Example 5

Form 3 Crystalline Potassium Salt of Compound A

A standard 0.5 N aqueous solution of KOH (1 equivalent) was added to a solution of Compound A (1 equivalent) in MeCN (0.05 M) and the mixture was stirred at room temperature for 15 minutes. The resulting solution was frozen in a −78° C. bath and then freeze dried to yield an amorphous potassium salt. A portion of the amorphous salt was then dissolved in hot EtOH (0.034 M) and within a few minutes material crystallized out. The mixture was allowed to stand at room temperature for 15 minutes and was then filtered and dried to yield a crystalline potassium salt.

$^1$H NMR of the first batch: (300 MHz, d6-DMSO) 11.70-11.20 (1H, broad s), 9.75 (1H, s), 7.33 (2H, dd, J=8.8, 5.8 Hz), 7.12 (2H, t, J=8.8 Hz), 4.44 (2H, d, 5.8 Hz), 3.40 (3H, s), 2.56 (3H, s), 1.70 (6H, s).

Figure 5:
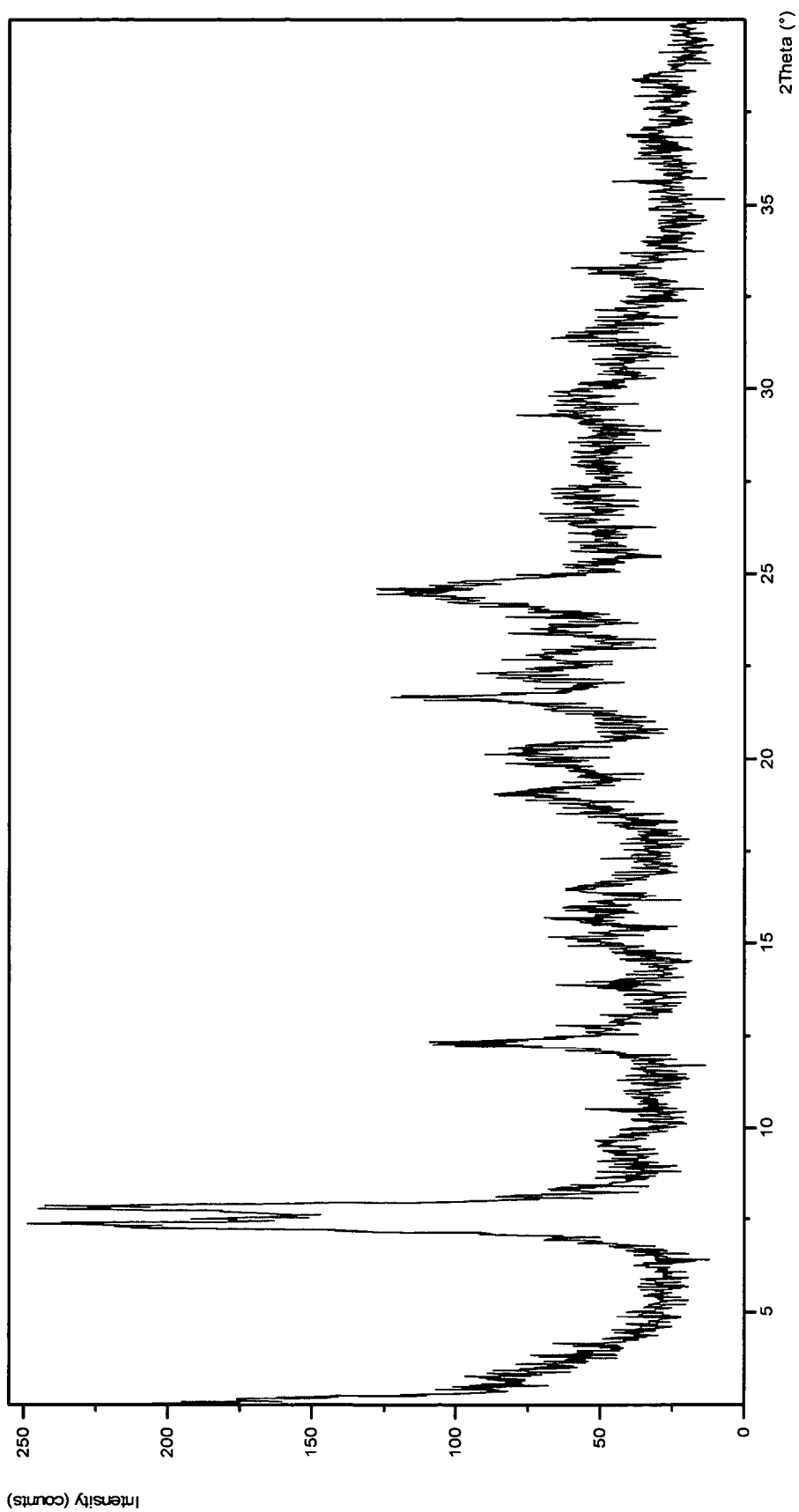
FIG. 5 is the X-ray powder diffraction pattern for the potassium salt of Compound A as prepared in Example 5.

An XRPD pattern of a crystalline K salt obtained in the manner described above was generated on a Philips Analytical X'Pert Pro X-ray powder diffractometer using a continuous scan from 2.5 to 40 degrees 2 Θ over about 2 minutes (i.e., 0.02° step size with 5 seconds/step), 2 RPS stage rotation, and a gonio scan axis. The XRPD pattern is shown in FIG. 5. 2Θ values and the corresponding d-spacings include the following:

| Peak No. | d-spacing (Å) | 2 Theta |
|---|---|---|
| 1 | 12.0 | 7.4 |
| 2 | 11.3 | 7.8 |
| 3 | 7.2 | 12.3 |
| 4 | 4.1 | 21.6 |
| 5 | 3.6 | 64.7 |

Figure 6:
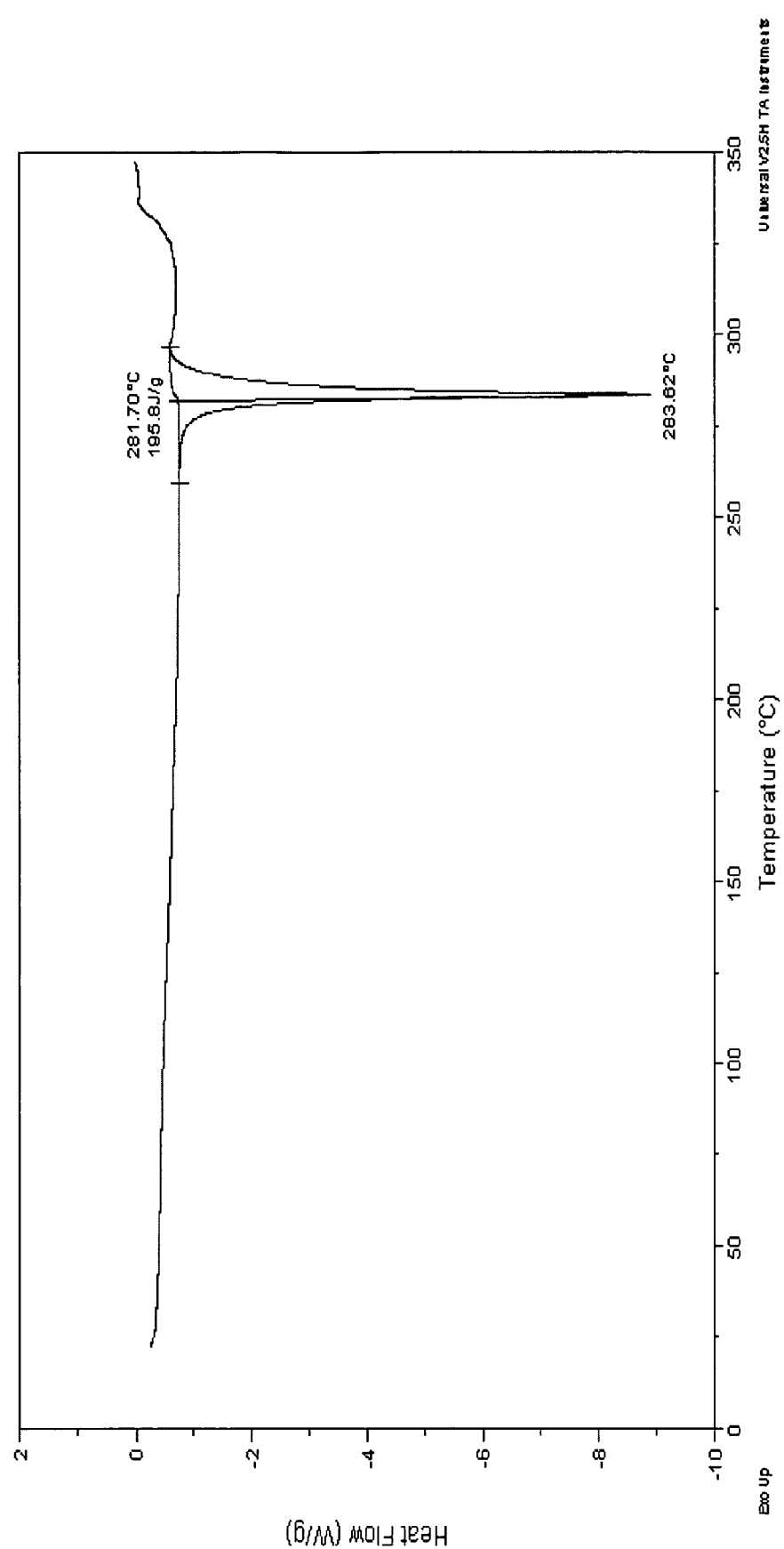
FIG. 6 is the DSC curve for the potassium salt of Compound A as prepared in Example 5.

K salt obtained in the manner described above was also analyzed by DSC using the same instrument and in the same manner as described in Example 2. The DCS curve, shown in FIG. 6, exhibited a single, sharp endotherm at about 284° C. (heat if fusion=195.8 J/gm). Thermogravimetric analysis done in the manner described in Example 2 above showed a loss of 0.5 wt. % during heating up to 200° C. Hygroscopicity data obtained in the same manner as described in Example 2 showed a 1% weight increase when equilibrated at 95% RH at 25° C. When equilibrated back down to 5% RH, the material returned to its dry weight. XRPD analysis of the material following its use in the hygroscopicity study showed that the material had not changed phases.

Example 6

Tablet Formulation Containing Form 1 Crystalline Potassium Salt of Compound A

Part A—

| Ingredient | Amount per Tablet (mg) | Amt per batch (wt. percent) |
|---|---|---|
| Compound A K salt[1] | 111.2 | 27.8 |
| (on free phenol basis) | (100) | (25.0) |
| microcrystalline cellulose (AVICEL PH-102) | 189.6 | 47.4 |
| lactose monohydrate | 63.2 | 15.8 |
| croscarmellose sodium | 12.0 | 3.0 |
| HPMC 2910 (6 centipoise) | 20.0 | 5.0 |
| magnesium stearate (intragranular) | 2.0 | 0.5 |
| magnesium stearate (extragranular) | 2.0 | 0.5 |

[1]Form 1 crystalline monopotassium salt of Compound A; conversion factor (including purity) = 1.112.

Compressed tablets containing 100 mg of Compound A on a free phenol basis were prepared by blending all of the ingredients listed above, except for the extragranular magnesium stearate, in a blender (Turbula® Type T2F shaker-mixer, Basel, Switzerland) for 10 minutes. Portions of the blended material weighing approximately 1 gram were compressed into compacts (or slugs) in a benchtop press (Auto Carver Model Auto "C", Catalog No. 3888, Carver, Inc., Wabash, Ind.) using 1×0.5 inch rectangular tooling to 12 MPa (4 KN). The slugs were then sized into granules by passing them through a sieve with 1 mm openings. The granules were blended with the extragranular magnesium stearate in the Turbula blender for 5 minutes, and the lubricated granules were compressed into tablets using the Auto Carver press with ¹³⁄₃₂-inch standard concave round tooling.

Part B—

| Ingredient | Amount per Tablet (mg) | Amt per batch (wt. percent) |
|---|---|---|
| Compound A K salt[1] | 110 | 27.5 |
| (on free phenol basis) | (100) | (25.0) |
| microcrystalline cellulose (AVICEL PH-102) | 175.2 | 43.8 |
| microcrystalline cellulose (AVICEL PH-105) | 9.2 | 2.3 |
| lactose monohydrate | 61.6 | 15.4 |
| croscarmellose sodium | 12.0 | 3.0 |
| HPMC 2910 (6 centipoise) | 20.0 | 5.0 |
| magnesium stearate (intragranular) | 4.0 | 1.0 |
| magnesium stearate (extragranular) | 8.0 | 2.0 |

[1]Form 1 crystalline monopotassium salt of Compound A; conversion factor (including purity) = 1.112.

Compressed tablets having the composition set forth in the above table were prepared using a procedure similar to that set forth in Part A.

Example 7

Tablet Formulation Containing Form 1 Crystalline Potassium Salt of Compound A

| Ingredient | Amount per Tablet (mg) | Amt per batch (wt. percent) |
|---|---|---|
| Compound A K salt[1] | 434.4 | 50.0 |
| (on free phenol basis) | (400) | (46.0) |
| microcrystalline cellulose (Avicel PH102) | 112.9 | 13.0 |
| lactose hydrous spray dried | 26.06 | 3.0 |
| anhydrous dibasic calcium phosphate | 73.85 | 8.50 |
| HPMC K4M | 26.06 | 3.0 |
| poloxamer 407 (micronized grade)[2] | 173.8 | 20.0 |
| sodium stearyl fumarate | 8.69 | 1.0 |
| magnesium stearate | 13.03 | 1.50 |

[1]Form 1 crystalline monopotassium salt of Compound A; conversion factor = 1.086.
[2]Obtained from BASF. Median particle size = 50 μm.

Compressed tablets containing 400 mg of Compound A on a free phenol basis were prepared by a roller compaction and tablet compression process train. Poloxamer 407, magnesium stearate, and sodium stearyl fumarate were pre-screened through No. 30 and No. 60 mesh size screens in succession, and then blended with all of the other ingredients, except for the extragranular magnesium stearate, in a Patterson-Kelly (PK) V-blender for 5 minutes. The blended material was then sieved through a No. 35 screen mesh to break up agglomerates, and the sieved material was then blended further in the same PK blender for about 15-20 minutes. The blend was then roller compacted using a Freund Type TF mini roller compactor at a roll pressure of 40 Kgf/cm², roll speed of 3 rpm and screw speed of 10 rpm. The resulting ribbon was milled in a small Quadro Comil fitted with a round impeller, screen size 39R (i.e., round hole size 0.039 inches; approximately mesh size No. 20) and operated at 1700 rpm. The resulting granules were then blended with 0.5% extragranular magnesium stearate in the PK blender for 5 minutes to produce the final blend. The lubricated granules were then compressed into tablets using a rotary tablet press with plain oval shaped tooling at a compression force necessary to achieve a tablet hardness of 16 to 20 kiloponds (i.e., 156.9 to 196.1 Newtons) as measured by using a Key model HT-300 hardness tester.

While the foregoing specification teaches the principles of the present invention, with examples provided for the purpose of illustration, the practice of the invention encompasses all of the usual variations, adaptations and/or modifications that come within the scope of the following claims.

What is claimed is:

1. An anhydrous crystalline potassium salt of Compound A, which is characterized by an X-ray powder diffraction pattern obtained using copper $K_\alpha$ radiation which comprises 2Θ values in degrees of 5.9, 20.0 and 20.6; wherein Compound A is of formula:

2. The anhydrous crystalline potassium salt of Compound A according to claim 1, which is further characterized by a differential scanning calorimetry curve, obtained at a heating rate of 10° C./min in a closed cup under nitrogen, exhibiting a single endotherm with a peak temperature of about 279° C.

3. The anhydrous crystalline potassium salt of Compound A according to claim 1, which is characterized by an X-ray powder diffraction pattern obtained using copper $K_\alpha$ radiation which comprises 2Θ values in degrees of 5.9, 12.5, 20.0, 20.6 and 25.6.

4. The anhydrous crystalline potassium salt of Compound A according to claim 3, which is further characterized by a differential scanning calorimetry curve, obtained at a heating rate of 10° C./min in a closed cup under nitrogen, exhibiting a single endotherm with a peak temperature of about 279° C.

5. The anhydrous crystalline potassium salt of Compound A according to claim 1, which is a monopotassium salt.

6. A pharmaceutical composition comprising an effective amount of a potassium salt of Compound A as recited in claim 1 and a pharmaceutically acceptable carrier.

7. A pharmaceutical composition which comprises the product made by combining an effective amount of a potassium salt of Compound A as recited in claim 1 and a pharmaceutically acceptable carrier.

8. A method of treating HIV infection, delaying the onset of AIDS, or treating AIDS in a subject in need thereof, which comprises administering to the subject an effective amount of a potassium salt of Compound A as recited in claim 1.

9. A process for preparing a crystalline potassium salt of Compound A as recited in claim 1, which comprises:
(A1-1) mixing an aqueous solution of a potassium base with a mixture comprising Compound A, water and a first amount of an alcohol to form a basic solution of Compound A and optionally filtering the solution; and
(A1-2) seeding the solution formed in Step A1-1 and optionally diluting the seeded solution with a second amount of the alcohol; or
(B1-1) seeding a mixture comprising Compound A and a first amount of an organic solvent selected from the group consisting of a halogenated alkane, a dialkyl ether, dialkoxyalkane, a cyclic ether or diether, a trialkylamine, a tertiary amide, an N-alkylpyrrolidone, a dialkyl sulfoxide and an alkanenitrile; and (B1-2) adding an aqueous solution of a potassium base to the seeded mixture of Step B1-1; and
(C1) ageing the seeded solution resulting from Step A1-2 or from Step B1-2, to provide the crystalline potassium salt of Compound A.

10. The process according to claim 9, wherein the process comprises:
(A1-1) mixing an aqueous solution of KOH with a mixture comprising Compound A, water and a first amount of ethanol to form a basic solution of Compound A and optionally filtering the solution;
(A1-2) seeding the solution formed in Step A1-1 and diluting the seeded solution with a second amount of ethanol to obtain a diluted, seeded solution; and
(C1) ageing the diluted, seeded solution of Step A1-2, to provide the crystalline K salt of Compound A.

11. The process according to claim 10, wherein:
Step A1-1 is conducted at a temperature in a range of from about 20 to about 30° C.;
Step A1-2 is conducted at a temperature in a range of from about 20 to about 30° C.;
Step C1 is conducted at a temperature in a range of from about 0 to about 20° C.;
in Step A1-1, the basic solution has a volume to volume ratio of ethanol to water in a range of from about 70:30 to about 30:70;
in Step A1-2, the diluted, seeded solution has a volume to volume ratio of ethanol to water of at least about 80:20;
seed crystals are employed in an amount in a range of from about 1 to about 5 wt. % based upon the total weight of Compound A; and
KOH is employed in an amount in a range of from about 0.9 to about 1.1 equivalents per equivalent of Compound A.

12. The process according to claim 9, wherein the process comprises:
(B1-1) seeding a solution comprising Compound A and acetonitrile;
(B1-2) adding an aqueous solution of KOH to the seeded solution formed in Step B1-1; and
(C1) ageing the solution of Step B1-2, to provide the crystalline K salt of Compound A.

13. The process according to claim 12, wherein:
Step B1-1 is conducted at a temperature in a range of from about 20 to about 30° C.;
Step B1-2 is conducted at a temperature in a range of from about 20 to about 30° C.;
Step C1 is conducted at a temperature in a range of from about 20 to about 30° C.;
the seeded solution obtained in Step B1-2 has a volume to volume ratio of acetonitrile to water of at least about 90:10;
seed crystals are employed in an amount in a range of from about 1 to about 5 wt. % based upon the total weight of Compound A; and
KOH is employed in an amount in a range of from about 0.9 to about 1.1 equivalents per equivalent of Compound A.

14. A process for preparing a crystalline potassium salt of Compound A as recited in claim 1, which comprises:
- (A2) adding:
  - (i) a feed solution comprising Compound A and (a) a first amount of a first solvent selected from the group consisting of a dialkyl ketone, a dialkyl ether, dialkoxy alkane, a cyclic ether or diether, a trialkylamine, a tertiary amide, an N-alkylpyrrolidone, a dialkylsulfoxide, and an alkanenitrile and (b) a first amount of a second solvent selected from the group consisting of an alcohol, an alkane, an alkyl ester of an alkylcarboxylic acid, and an aromatic hydrocarbon, and
  - (ii) a feed mixture comprising a potassium alkoxide base and a second amount of the second solvent,
- to a crystallizer containing seed crystals slurried in a solvent mixture comprising a second amount of the first solvent and a third amount of the second solvent to obtain a crystallization mixture; wherein at least a substantial portion of the feed solution and the feed mixture are added to the crystallizer concurrently; and
- (B2) ageing the crystallization mixture obtained in Step A2, to provide the crystalline potassium salt of Compound A.

15. The process according to claim 14, wherein the process comprises:
- (A2) adding a feed solution comprising Compound A, a first amount of acetonitrile, and a first amount of ethanol and a feed mixture which is a solution comprising potassium ethoxide and a second amount of ethanol to a crystallizer containing seed crystals slurried in a solvent mixture comprising a second amount of acetonitrile and a third amount of ethanol to obtain a crystallization mixture; wherein at least a substantial portion of the first and second solutions are added to the crystallizer concurrently; and
- (B2) ageing the crystallization mixture obtained in Step A2, to provide the crystalline potassium salt of Compound A.

16. The process according to claim 15, wherein
- in Step A2 potassium ethoxide is employed in an amount in a range of from about 0.9 to about 1.1 equivalents per equivalent of Compound A;
- Step A2 is conducted at a temperature in a range of from about 20 to about 30° C.;
- Step B2 is initially conducted at a temperature in a range of from about 30 to about 40° C., and then from about 20 to about 30° C. until completion;
- seed crystals are employed in an amount in a range of from about 10 to about 25 wt. %; and
- the crystallization mixture in Step A2 has a final solvent volume ratio of acetonitrile to ethanol in a range of from about 80:20 to about 20:80.

17. A process for preparing a crystalline potassium salt of Compound A as recited in claim 1, which comprises:
- (A3) adding (i) a first solution comprising Compound A and a first amount of a water-dissolving organic solvent selected from the group consisting of a dialkyl ketone, a dialkyl ether, dialkoxy alkane, a cyclic ether or diether, a trialkylamine, a tertiary amide, an N-alkylpyrrolidone, a dialkylsulfoxide, and an alkanenitrile, and (ii) a second solution comprising KOH and a first amount of water, to a crystallizer containing seed crystals slurried in a mixture comprising a second amount of the organic solvent and a second amount of water; wherein at least a substantial portion of the first and second solutions are added to the crystallizer concurrently; and
- (B3) ageing the crystallization mixture obtained in Step A, to provide the crystalline potassium salt of Compound A.

18. The process according to claim 9, wherein the potassium base employed in Step A1-1 or Step B1-2 comprises potassium hydroxide, potassium carbonate, potassium bicarbonate, or potassium alkoxide.

19. The process according to claim 9, wherein in Step A1-1 or Step B1-2 the potassium base is employed in an amount in a range of from about 0.1 to about 3 equivalents per equivalent of Compound A.

20. The process according to claim 9, wherein Steps A1-1 and A1-2 or Steps B1-1 and B1-2 are each conducted at a temperature in a range of from about 0 to about 60° C.

21. The process according to claim 9, wherein the basic solution formed in Step A1-1 has a volume to volume ratio of alcohol to water in a range of from about 80:20 to about 20:80.

22. The process according to claim 9, wherein, when the seeded solution is optionally diluted in Step A1-2, the diluted, seeded solution has a volume to volume ratio of solvent alcohol to water of at least about 60:40.

23. The process according to claim 9, wherein the solution resulting from Step B1-2 has a volume to volume ratio of organic solvent to water of at least about 70:30.

* * * * *